United States Patent [19]
Mills et al.

[11] Patent Number: 6,080,862
[45] Date of Patent: Jun. 27, 2000

[54] STEREOSELECTIVE SYNTHESIS OF ENDOTHELIN RECEPTOR ANTAGONISTS

[75] Inventors: Robert John Mills, Norristown; Conrad John Kowalski, Paoli; Li-Jeng Ping, Collegeville; Kerry Joseph Gombatz, West Chester, all of Pa.

[73] Assignee: SmithKline Beecham Corporation, Philadelphia, Pa.

[21] Appl. No.: 09/068,427

[22] PCT Filed: Nov. 8, 1996

[86] PCT No.: PCT/US96/18084

§ 371 Date: May 8, 1998

§ 102(e) Date: May 8, 1998

[87] PCT Pub. No.: WO97/17071

PCT Pub. Date: May 15, 1997

Related U.S. Application Data

[60] Provisional application No. 60/006,348, Nov. 8, 1995, and provisional application No. 60/006,347, Nov. 8, 1995.

[51] Int. Cl.[7] .................... C07D 221/04; C07D 317/48
[52] U.S. Cl. .................... 546/183; 549/434; 549/435; 549/448
[58] Field of Search .................... 549/434, 435, 549/448; 546/183

[56] References Cited

U.S. PATENT DOCUMENTS 5,389,620  2/1995  Ishikawa et al. .................... 514/80

FOREIGN PATENT DOCUMENTS

WO 93/08799  5/1993  WIPO .
WO 94/25013  11/1994  WIPO .
95/05374  2/1995  WIPO .

*Primary Examiner*—Johann Richter
*Assistant Examiner*—Tadfiq A. Solola
*Attorney, Agent, or Firm*—Linda E. Hall; Stephen A. Venetianer; Charles M. Kinzig

[57] ABSTRACT

The present invention is directed to a synthetic route for preparing endothelium receptor antagonists of formulae (7B) and (7A) and to the chiral intermediates

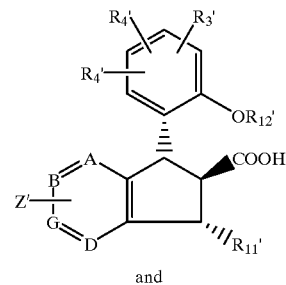

(7B)

and

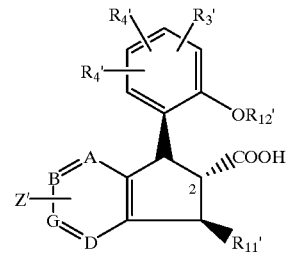

(7A)

22 Claims, No Drawings

STEREOSELECTIVE SYNTHESIS OF ENDOTHELIN RECEPTOR ANTAGONISTS

This Application claims the benefit of Provisional Application 60/006,348 Nov. 8, 1995 and the benefit of Provisional Application 60/006,347 Nov. 8, 1995.

FIELD OF THE INVENTION

The present invention relates to the stereoselective synthesis of aryl and heteroaryl ring-fused cyclopentane derivatives useful as endothelin receptor antagonists and to the preparation of chiral intermediates in the process.

BACKGROUND OF THE INVENTION

Endothelin (ET) is a highly potent vasoconstrictor peptide synthesized and released by the vascular endothelium. Endothelin exists as three isoforms, ET- 1, ET-2 and ET-3 (unless otherwise stated, "endothelin" shall mean any or all of the isoforms of endothelin). Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

Many studies suggest that endothelin receptor antagonists would offer a unique approach toward the pharmacotherapy of hypertension, renal failure, ischemia-induced renal failure, sepsis-endotoxin-induced-renal failure, prophylaxis and/or treatment of radio-contrast-induced renal failure, acute and chronic cyclosporin-induced renal failure, cerebrovascular disease, myocardial ischemia, angina, heart failure, asthma, pulmonary hypertension, pulmonary hypertension secondary to intrinsic pulmonary disease, atherosclerosis, Raynaud's phenomenon, ulcers, sepsis, migraine, glaucoma, endotoxin shock, endotoxin-induced multiple organ failure or disseminated intravascular coagulation, cyclosporin induced renal failure and as an adjunct in angioplasty for prevention of restenosis, diabetes, preclampsia of pregnancy, bone remodeling, kidney transplant, male contraceptives, infertility and priaprism and benign prostatic hypertrophy.

Recent publications disclose that aryl and heteroaryl ring-fused cyclopentane derivatives have utility as endothelin receptor antagonists. See, e.g., International application Number PCT/US94/04603 (WO 94/25013) and U.S. Pat. No. 5,389,620. These particular publications also disclose synthetic approaches to the preparation of specific aryl and heteroaryl ring-fused cyclopentane derivatives, where those derivatives may function as endothelin receptor antagonists.

Unfortunately, the synthetic methods disclosed in the literature for making aryl and heteroaryl ring-fused cyclopentane derivatives do not provide for the desired products in high yield. Instead, the methods discussed in the literature require many steps, which are laborious and consequently expensive to conduct. Furthermore, when known methods provide for enantiomerically or diastereomerically pure products, they rely on chromatography to separate the various stereoisomers. Chromatography is far from a preferred approach in the preparation of isomerically pure materials on a commercial scale. Exemplary of this approach is the synthesis of (+) (1S,2R,3S) 3-(2-carboxymethoxy-4-methoxyphenyl)-1-(3,4-methylenedioxyphenyl)-5-(prop-1-yloxy)indane-2-carboxylic acid and (+) (1S,2R,3S) 3-[2-(2-hydroxyeth-1-yloxy)-4-methoxyphenyl-1-(3,4-methylenedioxyphenyl)-5-(prop-1-yloxy)indane-2-carboxylic acid, which as set forth in WO 94/25013, is multi-step, low yielding and relies upon a chromatographic resolution of a racemic intermediate in order to prepare the named compounds in optically pure form.

A technique that needs to be developed in the synthetic art is the use of chiral aryl Grignard reagents. Chiral aryl Grignard reagents have seen some use as intermediates for the preparation of diastereomerically and enantiomerically pure compounds. Such chiral aryl Grignard reagents have been prepared, for example, from chiral oxazolidines derived from aryl aldehydes. See, e.g., Real, S. D. et al., U.S. Pat. No. 5,332,840 and *Tet. Lett.,* 34, 8063–8066, 1993; Agami, C. et al., *Tetrahedron,* 41, 537–540, 1985; and Takahashi, H. et al., *Synthesis,* 681–682, 1992. Depending upon the reaction conditions, good to excellent diastereoselectivity has been reported for the addition of such chiral Grignard species to aldehydes, ketones and anhydrides. Aryl aldehydes have also been converted to chiral aryl Grignard reagents through formation of a homochiral acetal group adjacent to the Grignard reactive site. Such chiral materials have also been utilized in diastereoselective additions to carbonyl groups. See, e.g., Yamamoto, H. et al., *Bull. Chem. Soc. Jap.,* 62, 3736–3738, 1989.

However, the utility of chiral aryl Grignard reagents derived from chiral aryl ethers, wherein a phenol has been protected with a suitable chiral protecting group has seen little, if any, practical application. In one example where a chiral aryl Grignard reagent was derived from a chiral aryl ether, and then reacted with a carbonyl compound, only a slight diastereoselectivity for the reaction might be inferred, but was not conclusively established. See Ronald et al., *J. Org. Chem.,* 45, 2224–2229, 1980.

Thus, the preparation of chiral aryl Grignard reagents derived from chiral aryl ethers, and their use in the preparation of diastereomerically and enantiomerically pure compounds in the synthesis of aryl and heteroaryl ring fused cyclopentane derivatives, has not yet been established as viable synthetic methodology. Such methodology has utility in, for example, the preparation of endothelin receptor antagonists as disclosed in WO/9308799-A1 and U.S. Pat. No. 5,389,620, both of which are incorporated by reference herein, which to date have been prepared only via racemic mixtures of compounds, where chiral chromatography is necessary to obtain enantiomerically pure compounds. See, e.g., WO/9308799-A1. There is thus a need in the art to exploit chiral aryl Grignard reagents in the synthetic methodology useful in the preparation of enantiomerically and diastereomerically pure compounds that may be converted to endothelin receptor antagonists, and where the compounds are in enantiomerically or diastereomerically pure form without the need to resort to time-consuming and expensive chromatography.

Moreover, as explained more fully below, a preferred stereoselective synthesis of aryl and heteroaryl ring-fused cyclopentane derivatives will be able to place substituents at the three contiguous, non-ring fused carbons of the cyclopentane ring in a stereocontrolled manner. Furthermore, a preferred synthetic method will proceed in high overall yield, with minimal need to isolate and purify intermediates. This is a sophisticated challenge which is not met by any currently recognized synthetic methods.

There is thus a need in the art for an efficient synthetic method to prepare aryl and heteroaryl ring-fused cyclopentane derivatives, in completely or substantially enantiomerically or diastereomerically pure form, without the need to resort to chromatographic purification. In particular, there is a need in the art for methods to prepare (+) (1S,2R,3S) 3-(2-carboxymethoxy-4-methoxyphenyl)-1-(3,4-methylenedioxyphenyl)-5-(prop-1-yloxy)indane-2-carboxylic acid and (+) (1 S,2R,3S) 3-[2-(2-hydroxyeth-1-yloxy)-4-methoxyphenyl]-1-(3,4-methylenedioxyphenyl)-5-(prop-1-yloxy)indane-2-carboxylic acid, and pharmaceutically acceptable salts thereof, in an efficient and economical manner.

The numerous advantages of the presently invented processes and intermediates will become apparent upon review of the following description.

SUMMARY OF THE INVENTION

The present invention is directed to a process for preparing aryl and heteroaryl ring fused cyclopentane derivatives of the formula:

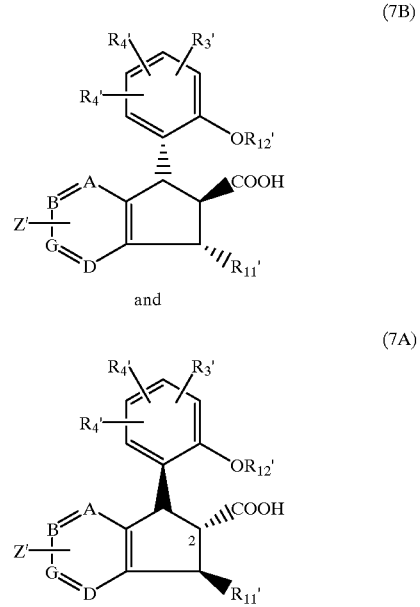

or pharmaceutically acceptable salts thereof
wherein $R_3'$, $R_4'$ and $R_5'$ are independently hydrogen, $C_1$–$C_6$ alkyl, $C_1$–$C_8$ alkoxy, or hydroxy;

$R_{12}'$ is $(CH_2)_2OH$ or $(CH_2)p\ CO_2H$;

p is an integer 1–3;

A, B, G and D are each carbon atoms or one of A, B, G and D is a nitrogen atom, and the remainder are carbon atoms;

Z' is hydrogen, hydroxy, $C_1$–$C_5$ alkoxy or $C_1$–$C_5$ alkyl; and $R_{11}'$ is unsubstituted 3,4-methylenedioxyphenyl or substituted 3,4-methylenedioxyphenyl, wherein the substituent is on the phenyl ring and is $C_1$–$C_5$ alkyl, $C_1$–$C_5$ alkoxy or hydroxy.

These compounds of Formulae 7A and 7B are useful as endothelin receptor antagonists. Examples of compounds useful is endothelin receptor antagonists that fall within the purview of these formula include (+)-(1S, 2R, 3S)-3-(2-carboxymethoxy-4-methoxyphenyl)-1-(3,4-methylenedioxyphenyl)-5-propoxyindane-2-carboxylic acid and (+)-(1S, 2R, 3S)-3-[2-(2-hydroxyeth-1-yloxy)-4-methoxyphenyl]-1-(3,4-methylenedioxyphenyl)-5-propoxyindane-2-carboxylic acid. As described hereinbelow, both compounds of Formula 7A and 7B are prepared by analogous processes. An examplary procedure for the preparation of compound 7A is depicted in Schemes 1–4, but the scheme is equally applicable for the preparation of a compound of Formula 7B.

In Scheme 1, an ortho-halo phenolic compound of Formula (I) wherein $R_1$ is halide, is reacted with a chiral electrophile of Formula (2) designated "$R_2L$" wherein "L" is a leaving group. This reaction affords an aryl ether where the phenolic group is protected by a chiral auxiliary ($R_2$) ortho to the halide ($R_1$) on a benzene ring, as represented by Formula (3). In the next step, the aryl halide of Formula (3) is converted to a reactive organometallic intermediate which in turn is reacted with a cyclopentenone of Formula (4) to provide a mixture of diastereomeric carbinols having Formulas (5A) and (5B). One of the carbinols (5A) or (5B), denoted the predominant diastereomer, will typically be formed in diastereomeric excess due to the influence of the chiral auxiliary ($R_2$). In a final step of Scheme 1, the mixture of diastereomeric carbinols may be subjected to a crystallization process to provide the predominant isomer in essentially pure form.

The diastereomerically-related compounds (5A) and (5B) as shown in Scheme 2, are stereoselectively hydrogenated to afford a composition comprising diastereomerically-related compounds (6A) and (6B). The mixture of compounds of Formulae (6A) and (6B) may optionally be subjected to a crystallization process in order to provide a single one of the diastereomers in essentially pure form.

6A is utilized to prepare 7A by two different processes, as shown in Scheme 3. According to Route (B) in Scheme 3, and exemplified more fully in Scheme 4, a diastereomerically pure compound of Formula (6A) is converted to a compound of Formula (13A) via a compound of Formula (11A) by hydrolysis and epimerization of the carboxylate ester at C2 followed by cleavage of the chiral aryl ether component and re-esterification of the carboxylate group at C2. A compound of Formula (13A) is then alkylated to afford an enantiomerically pure compound of Formula (14A) which is saponified to afford enantiomerically pure endothelin receptor antagonists of Formula (7A).

Alternatively, according to Route (A) chemistry in Scheme 3, a diastereomerically pure compound of Formula (6A) is converted to a compound of Formula (8A) by cleavage of the chiral aryl ether $OR_2$ group. Compounds of Formula (8A) are then alkylated to afford enantiomerically pure compounds of Formula (9A) which is then saponified to afford enantiomerically pure endothelin receptor antagonists of Formula (7A).

In the formulae in the various schemes, $R_3$, $R_4$ and $R_5$ are independently hydrogen, $C_1$–$C_6$ alkyl, $C_1$–$C_8$ alkoxy, halide or protected hydroxy;

$R_1$ is halide, especially bromide, chloride, or iodide;

$R_2$ is selected from the group consisting of anomers, enantiomers, and diestereomers of (1) carbohydrates and derivatives thereof, (2) terpenes and derivatives thereof and (3) amino acids and derivatives thereof, L is a leaving group;

A, B, G and D are independently carbon atoms or one of A, B, G and D is a nitrogen atom and the remainder are a carbon atoms;

Z is hydrogen, protected hydroxy, $C_1$–$C_5$ alkoxy or $C_1$–$C_5$ alkyl;

$R_{11}$ is unsubstituted 3,4-methylenedioxyphenyl or substituted 3,4-methylenedioxyphenyl wherein the substituent is on the phenyl ring and is $C_1$–$C_5$ alkyl, $C_1$–$C_5$ alkoxy or protected hydroxy;

$R_{10}$ is $C_1$–$C_5$ alkyl;

$R_{12}$ is $(CH_2)_2OH$ or $(CH_2)p\ CO_2R_{13}$;

$R_{13}$ is $C_1$–$C_5$ alkyl or hydrogen; and p is an integer from 1 to 3.

Another aspect of the present invention is directed to synthetic methods useful in preparing novel intermediates, such as, for example compounds 3, 5A, 5B, 6A, 6B, 8A, 8B, 9A, 9B, 11A, 11B, 13A, 13B and 14A, and 14B identified hereinbelow.

A particularly preferred aspect of the invention is directed to synthetic methods useful in preparing novel intermediates that may be converted to (+) (1S,2R,3S)-3-(2-carboxymethoxy-4-methoxyphenyl]-1-(3,4-methylenedioxyphenyl)-5-(prop-1-yloxy)indane-2-carboxylic acid and (+) (1S,2R,3S)-3-[2-(2-hydroxyeth-1-yloxy)-4-methoxyphenyl]-1-(3,4-methylenedioxyphenyl)-5-(prop-1-yloxy)indane-2-carboxylic acid and pharmaceutically acceptable salts thereof.

Another aspect of the present invention is directed to the novel intermediates useful in the preparation of the compounds of Formulae 7A and 7B.

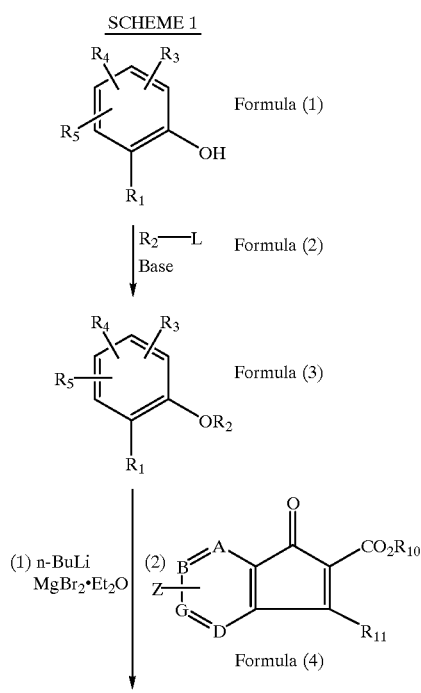

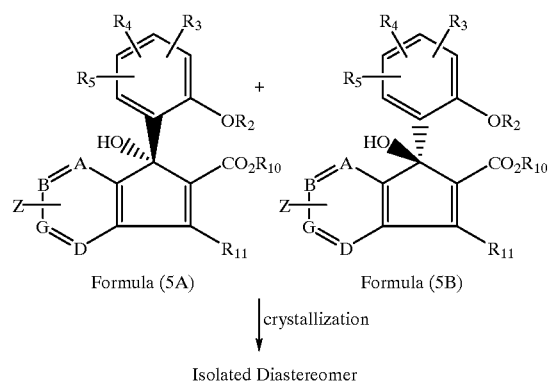

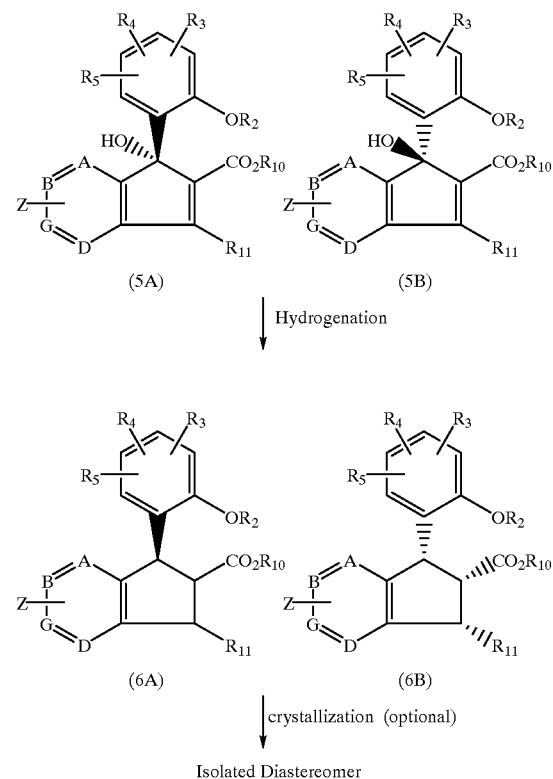

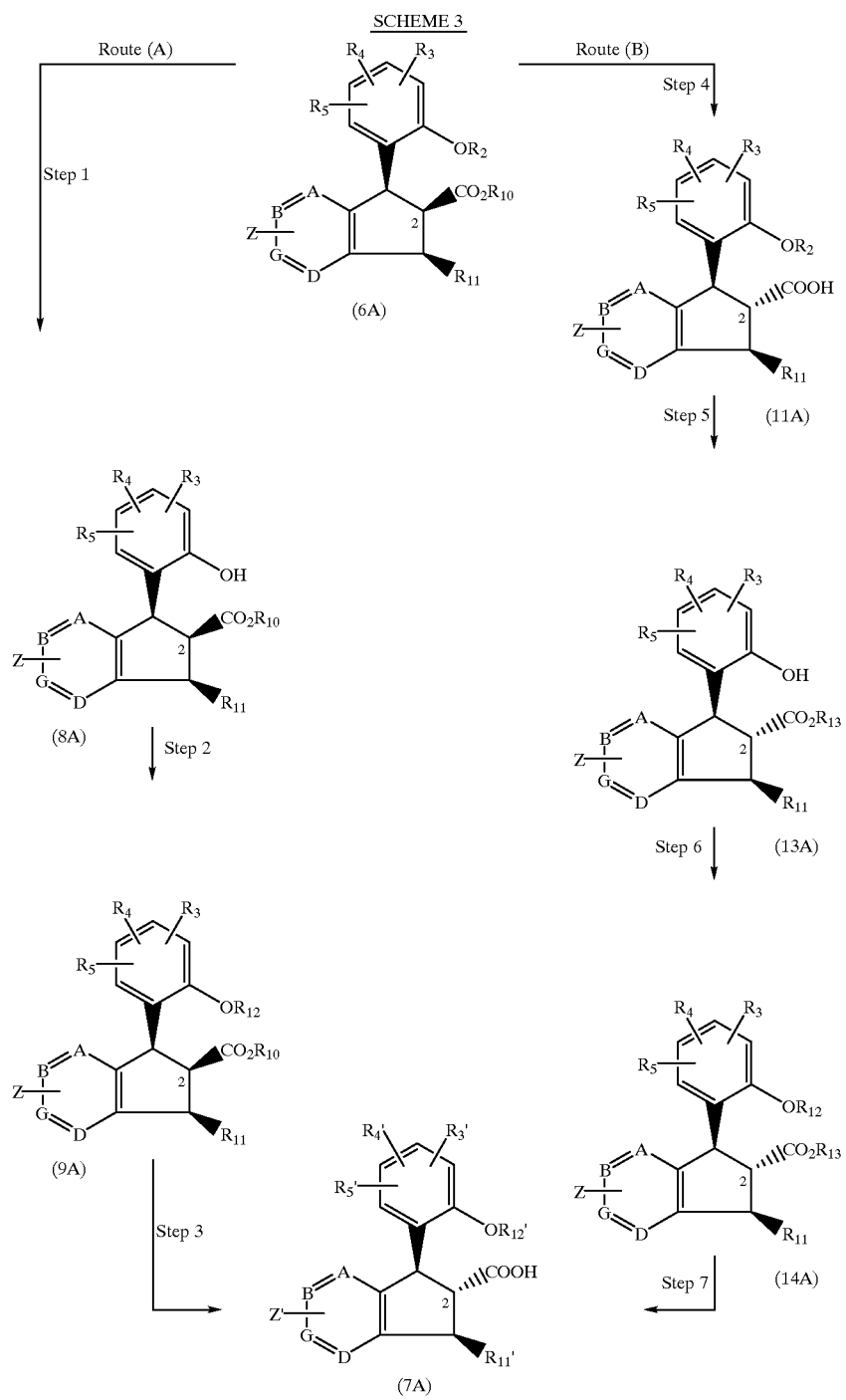

SCHEME 4

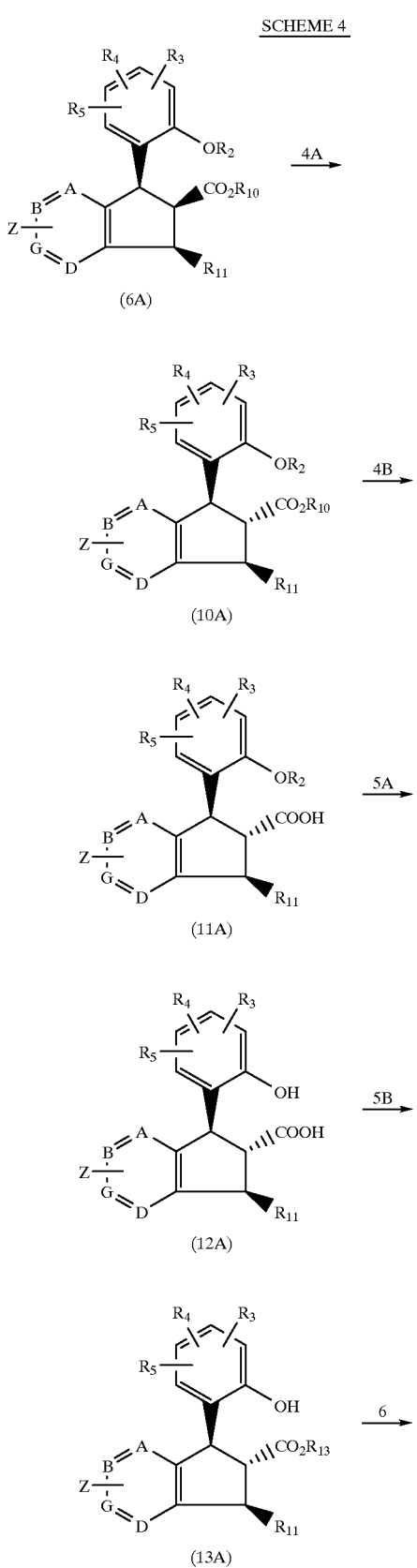

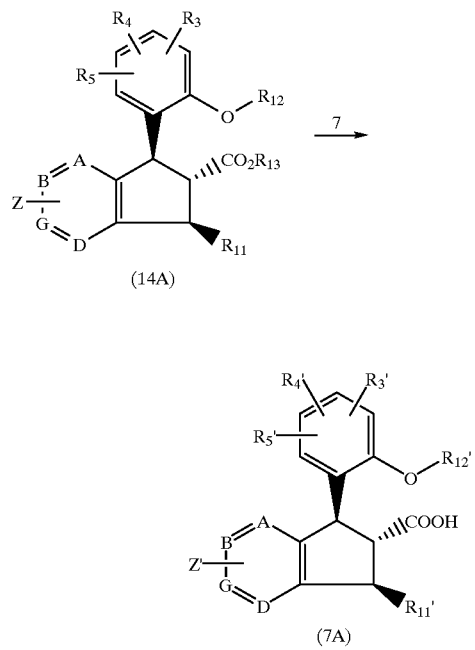

DETAILED DESCRIPTION OF THE INVENTION

As used herein and unless designated to the contrary, the term alkyl, when used alone or in combination, refers to an alkyl group which may be straight chained or branched. Preferred alkyl groups contain 1–8 carbon atoms, and even more preferred alkyl groups contain 1–6 carbon atoms. It is even more preferred that the alkyl group contains 1–3 carbon atoms, with methyl being the most preferred. Examples include methyl, ethyl, n-propyl, isopropyl, n-butyl, sec-butyl, isobutyl, t-butyl, n-pentyl, amyl, hexyl and the like.

The term alkoxy, when used alone or in combination, refers to o-alkyl. The preferred alkoxy group contains 1–3 carbon atoms.

The term halide refers to fluoride, bromide, chloride, or iodide, with bromide and chloride being the most preferred halides.

The term "protected hydroxyl" as used herein and throughout this specification means hydroxyl groups that have been reacted with appropriate protecting groups, where appropriate protecting groups for hydroxyl groups are well known in the art. Protecting groups which can be utilized are described in Greene, "Protecting Groups in Organic Synthesis", 1991, John Wiley and Sons, Inc., the contents of which are incorporated herein by reference. For example, in the case of simple phenolic hydroxyls, a suitable method of protection is the transformation of the hydroxyl groups to an aryl ether, e.g., methyl ether, methoxymethyl ether, benzyloxy methyl ether or cyclopropyl methyl ether. In the case of catechols (dihydroxy benzene), suitable protection thereof may be as a cyclic ether, for example, as a methylene acetal, an acetonide derivative or cyclohexylidene ketal.

The preferred $R_1$ groups are iodo, and especially bromo and chloro.

The preferred $R_3$, $R_4$ and $R_5$ as well as $R_3'$, $R_4'$ and $R_5'$ groups are independently hydrogen, $C_1-C_6$ alkyl, or $C_1-C_8$ alkoxy. It is more preferred that $R_3$, $R_4$ and $R_5$ and $R_3'$, $R_4'$ and $R_5'$ are independently hydrogen or $C_1-C_8$ alkoxy. It is even more preferred that $R_3$ and $R_5$ and $R_3'$ and $R_5'$ are hydrogen and $R_4$ and $R_4'$ are alkoxy, as defined herein, especially methoxy. Furthermore, it is preferred that $R_4$ and $R_4'$ are each para to $R_1$ and $R_1'$, respectively and it is most preferred that $R_4$ is alkoxy and is para to $R_1$ and that $R_4'$ is alkoxy and para to $R_1'$.

The preferred values of L are halide, especially chlorides, iodides and bromides, tosylates, and mesylates.

As defined herein, A, B, G and D, are either all carbon atoms or one of them is a nitrogen atom. If one is a nitrogen atom, it is preferred that the nitrogen atom be present in the one-position, i.e., it is preferred that D be a nitrogen atom. However, it is more preferred that A, B, G and D are all carbon atoms.

The ring containing A, B, G and D may either be substituted or unsubstituted. It is preferred that the ring is substituted. The preferred values of Z and Z' are lower alkyl or lower alkoxy, and especially preferred values of Z and Z' are lower alkoxy. Moreover, it is preferred that Z and Z' are substituted on B.

The preferred $R_{11}$ substituent is unsubstituted 3,4-methylenedioxyphenyl.

The preferred value of p is 1 or 2.

The preferred values of the other substituents will be discussed, infra.

In comparing the formulae of 7A (or 7B) with the other structures hereinabove, it is noted that $R_3$ and $R_3'$, $R_4$ and $R_4'$, $R_5$ and $R_5'$, Z and $Z_1'$, and $R_{11}$ and $R_{11}'$ each have similar definition. Except when $R_3$, $R_4$, $R_5$, $R_{11}$ and Z are a protected hydroxy, the definitions of $R_3$, $R_4$, $R_5$, $R_{11}$ and Z are the same as $R_3'$, $R_4'$, $R_5'$, $R_{11}'$ and $Z_1'$ respectively. It is noted that during the reaction conditions described herein, the hydroxy group if left unprotected, will be reactive. However, in the final product, 7A or 7B, the hydroxy group is no longer required to be protected. Thus, if the OH group are protected, it is preferred that at the end of the sequence of reactions, the protecting group be removed. Techniques for removing hydroxy protecting groups are well known in the art and are described in, e.g., Greene referred to hereinabove.

$R_{12}$ and $R_{12}'$ also have similar definitions. Both $R_{12}$ and $R_{12}'$ are $(CH_2)_2$ OH. However, $R_{12}$ may also be $(CH_2)p$ COOH. In other words, $R_{12}$ may also be an ester substituent, which, as described hereinbelow, is hydrolyzed to form the corresponding acid, i.e., $R_{12}'$.

Consequently, there is a relationship between the values $R_3-R_5$, and $R_3'-R_5'$, Z and Z', $R_{11}$ and $R_{11}'$ and $R_{12}$ and $R_{12}'$. For example, if $R_3$, $R_4$, $R_5$ or Z is a protected hydroxy, then the corresponding value of $R_3'$, $R_4'$, $R_5'$ and $Z_1'$, respectively is hydroxy; on the other hand, if $R_3$, $R_4$ or $R_5$, or Z is other than protected hydroxy, then each of $R_3$, $R_4$, $R_5$ and Z have the same value as the corresponding $R_3'$, $R_4'$, $R_5'$ and $Z_1'$. Moreover, if $R_{11}$ contains a protected hydroxy substituent, then $R_{11}'$ contains a hydroxy substituent; on the other hand, if $R_{11}$ is different than protected hydroxy, then $R_{11}$ and $R_{11}'$ are the same. Finally, if $R_{12}$ is $(CH_2)_2OH$, then $R_{12}'$ is $(CH_2)_2OH$; however, if $R_{12}$ is $(CH_2)pCO_2R_{13}$, then $R_{12}'$ has the corresponding value $(CH_2)pCOOH$.

The compounds 7A and 7B are synthesized in accordance with the present invention, as described hereinbelow.

As described herein, the ortho-halo phenolic compounds of Formula I hereinbelow are useful precursors in the inventive methodology of the present invention. In Formula (1), $R_1$ is chloride, bromide or iodide, and is bonded to a benzene ring. A hydroxy group is located in an ortho position to $R_1$. Thus, the compounds of Formula (1) may be denoted as ortho-halo phenolic compounds.

Formula (I)

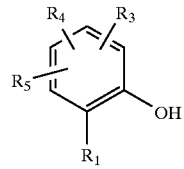

As described hereinabove, the moieties $R_3$, $R_4$, and $R_5$ in Formula (1) and in any of the Formulae disclosed herein that contain any of $R_3$, $R_4$, or $R_5$, are independently hydrogen, $C_1-C_6$ alkyl protected hydroxy or $C_1-C_8$ alkoxy. There are preferably no electrophilic centers on the compound of Formula (1) susceptible to attack by a phenolate anion under the preferred reaction conditions described below.

Specifically preferred ortho-halo phenolic compounds of Formula (1) is 2-chlorophenol, while an especially preferred compound of Formula (1) is 2-bromo-5-methoxyphenol, which is also known as 4-bromo-3-hydroxyanisole. Many suitable ortho-halo phenolic compounds are available from commercial supply houses, e.g., Aldrich Chemical Company (Milwaukee, Wis.). The preparation of 2-bromo-5-methoxyphenol is described in, e.g., de Paulis, T. et al., *J. Med. Chem.*, 28, 1263–1269, 1985.

Chiral electrophiles useful in the inventive methodology are represented by the Formula (2).

$R_2$-L            Formula (2)
Base

In Formula (2), the designation "L" represents a leaving group. As used herein, the term "leaving group" denotes an atom or atomic arrangement that is sufficiently stable in anionic form to detach from a carbon atom in response to nucleophilic attack at that carbon by a phenolic oxygen atom. Exemplary leaving groups include chloride, bromide and iodide. Many hydroxyl derivatives, e.g., derivatives prepared by the conversion of a hydroxyl group into an ester of a relatively strong acid, are leaving groups according to the invention. Exemplary hydroxyl group derived leaving groups include, without limitation, para-toluenesulfonyl ester (tosylate group), or methanesulfonyl ester (mesylate group) and the like. Chloride is a preferred leaving group "L" according to the invention.

In addition to a leaving group, the compounds of Formula (2) have an $R_2$ moiety, where the $R_2$ moiety has at least one chiral center, and the leaving group "L" is bonded to the $R_2$ moiety.

Suitable $R_2$ moieties according to the invention include, but are not limited to, the anomers, enantiomers and diastereomers of (1) carbohydrates and derivatives thereof including oligosaccharides, (2) terpenes and derivatives thereof including diterpenes and sesquiterpenes, and (3) amino acids and derivatives thereof including polypeptides. Preferably, the heteroatom(s) in $R_2$ is nitrogen, oxygen and/or sulfur, with oxygen in the form of one or more ether groups, as in carbohydrates and derivatives thereof, being most preferred.

Preferred carbohydrates and derivatives thereof that form the $R_2$ moiety include, but are not limited to, the furanose or pyranose forms of any of D-sugars, especially D-glucose, D-mannose and D-galactose, including oligomers thereof, also known as oligosaccharides. The carbohydrate derivatives preferably have all of their free hydroxyl groups in protected form. Preferably, the hydroxyl groups in protected form are unreactive with base or nucleophiles, such as an acetonide group (isopropylidene ketal) or benzyl or paramethoxybenzyl groups, and the like.

Preferred compounds of Formula (2) derived from terpenes or derivatives thereof include, but are not limited to, (−)-isopinocamphyl chloromethyl ether, (+)-isopinocamphyl chloromethyl ether, (1R,2S,5R)-chloromethyl-(−)-menthol, (1S,2R,5S)-chloromethyl-(+)-menthol, (−)-chloromethyldicyclohexylsulfamoyl-D-isoborneol and (+)-chloromethyldicyclohexylsulfamoyl-L-isoborneol and the like. While the aforelisted terpene-derived compounds of Formula (2) have a chloride leaving group, other leaving groups as previously defined may be substituted for the chloride according to the invention.

Preferred compounds of Formula (2) derived from amino acids or derivatives thereof include, but are not limited to, 2-chloromethyl-4-(S)-$C_{1-5}$alkyl oxazoline wherein $C_{1-5}$alkyl is preferably isopropyl, 2-chloromethyl-4-(R)-$C_{1-5}$ alkyl oxazoline wherein $C_{1-5}$alkyl is preferably isopropyl, 2-chloromethyl-4-(S)-$C_{6-12}$aryl oxazoline where $C_{6-12}$aryl is preferably phenyl but may also be $C_{1-5}$ alkyl-substituted phenyl or naphthyl, 2-chloromethyl-4-(R)-$C_{6-12}$aryloxazoline where $C_{6-12}$aryl is preferably phenyl but may also be alkyl-substituted phenyl or naphthyl, and the like. While the aforelisted preferred amino acid derived compounds of Formula (2) have a chloride leaving group, other leaving groups as previously defined may be substituted for the chloride according to the invention.

It is preferred that $R_2$ is a carbohydrate in the D-form. Particularly in the case where the $R_2$ moiety is a carbohydrate, but in other appropriate instances as well, the hydroxyl groups of $R_2$ may need to be protected from undesired reactions, i.e., the hydroxyl groups may need to be a "protected hydroxyl" group as that term has been previously defined herein. A preferred compound of Formula (2) is known as 2,3:5,6-di-O-isopropylidene-α-D-mannofuranosyl chloride and has the Formula (2A) shown below. The β-anomer, i.e., 2,3:5,6-di-O-isopropylidene-β-D-mannofuranosyl chloride (not shown) is another preferred compound of Formula (2).

(2A)

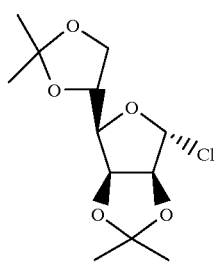

Compounds of Formula (2) are known in the chemical literature; see e.g., Ronald et al., *J. Org. Chem.* 1980, 45, 2224–2229. The compound of Formula (2A) can be prepared from diacetone-D-mannose according to procedures described in Nicolaou, K. C., et al., *Tet. Lett.*, 25, 2295 (1984) and references cited therein, where the Nicolaou reference is incorporated herein by reference.

According to the invention, compounds of Formula (1) and (2) are contacted in the presence of base, preferably in the further presence of solvent, to prepare a compound of Formula (3). Suitable bases include one or more of the alkali metal hydroxides and alkoxides, including lithium hydroxide, sodium hydroxide and potassium hydroxide, and $C_{1-5}$alkoxides such as sodium $C_{1-5}$alkoxides including sodium ethoxide, and potassium $C_{1-5}$alkoxides including potassium t-butoxide, and the like. Other suitable bases include tertiary amines such as DBU (1,8-diazobicyclo[5,4,0]undec-7-ene); alkali metal hydrides such as sodium hydride; alkali metal amides, such as lithium bis (trimethylsilylamide) and alkali; metal organometallics, wherein the organo moiety preferably contains 1–5 carbon atoms, such as n-butyl lithium, sec-butyl lithium and t-butyl lithium. Preferred bases include lithium hydroxide, sodium hydroxide, potassium hydroxide, sodium $C_{1-5}$alkoxide, potassium $C_{1-5}$alkoxide, DBU, sodium hydride, potassium hydride, lithium bis(trimethylsilylamide), n-butyl lithium, t-butyl lithium and sec-butyl lithium. More preferred bases include potassium t-butoxide, sodium hydride and DBU.

The solvent useful for the preparation of the Formula (3) compound should be inert to reaction with strong base, and be capable of dissolving the Formula (1) and Formula (2) compounds. Suitable solvents include one or more of aliphatic polyether, tetrahydrofuran (THF), toluene, diethyl ether and methyl t-butyl ether. Preferred solvents include 1,2-dimethoxyethane, diglyme also known as di-ethylene glycol dimethyl ether, which is a preferred aliphatic polyether, toluene, and the like.

According to a preferred process of the invention, a compound of Formula (1) is dissolved in a solvent under an inert atmosphere and cooled to about 0° C. to about 25° C. A base is then added with stirring, for sufficient time, for example, about 15 minutes to form the corresponding phenoxide, to which a compound of Formula (2) is added gradually. At least about 1 molar equivalent of base is preferably added per mole of halo-phenol compound of Formula (1), and preferably between about 1.0 molar and about 1.5 molar equivalents of base are added per mole of compound of Formula (1) in order to obtain a high yield of the desired product. The compounds of Formulae (1) and (2) may be contacted in equimolar or nonequimolar amounts. Whichever of the compounds of Formulas (1) or (2) is the least expensive is preferably present in molar excess relative to the other compound. When a compound of Formula (1) is dissolved in a solvent prior to contact with base, the compound is suitably dissolved at a concentration of from about 0.1 to about 10 molar, preferably from about 0.3 to about 3 molar.

The reaction mixture comprising solvent, base and compounds of Formulae (1) and (2) may be warmed to a temperature effective to form the resulting product. Preferably the temperature is in the range of about room temperature to about the reflux temperature of the solvent or solvent mixture employed in the reaction. Preferably, a reaction temperature of about 50° C. to about 120° C. is employed, and more preferably a reaction temperature of about 80° C. to about 90° C. is employed. The reactants are preferentially heated and maintained at temperatures sufficient for an appropriate amount of time until the formation of the compound of Formula (3) is essentially complete. A reaction time of about one to about five hours is typically necessary. The product mixture comprising the compound of Formula (3) may be worked-up in a typical manner, as known to one of ordinary skill in the art. A preferred work-up method is to add water to the product mixture and then extract the compound of Formula (3) into a water-immiscible solvent. Traces of residual compound of Formula (1) may be removed by simply washing the organic extract with dilute aqueous sodium hydroxide solution.

Thus, under the most preferred reaction conditions, compounds of Formula (1) and Formula (2) are contacted in the presence of a solvent such as an aliphatic polyether, tetrahydrofuran, toluene, diethyl ether and methyl t-butyl ether or mixtures thereof, and a base such as alkali metal hydroxide, alkali metal $C_{1-5}$alkoxide, alkali metal hydride, alkali metal amide, alkali metal organometallic or tertiary amine, at a reaction temperature of from about room temperature to about the reflux temperature of the solvent or solvent mixture. More preferably, the solvent is 1,2-dimethoxyethane, tetrahydrofuran or toluene, the base is sodium hydride, potassium t-butoxide or DBU, and the reaction temperature is from about 50° C. to about 110° C.

The process of the invention offers the advantage that further synthetic manipulation of the compound of Formula (3) can be accomplished without the need to isolate and purify the compound of Formula (3). Thus, after the compound of Formula (3) has been extracted into a water-immiscible solvent as described above, the solution of the Formula (3) compound may be used directly in, e.g., the synthetic scheme outlined in Scheme 1. Alternatively, the compound of Formula (3) may be isolated in purified form by techniques known to the skilled artisan, such as, e.g., distillation, crystallization and/or chromatography.

Alternatively, and in a similar manner, the compound of Formula (1) may be added to a solution of a base, and then the compound of Formula (2) added to the mixture of base and Formula (1) compound. Less preferably, the compounds of Formulae (1) and (2) can be combined and then base added to the combination.

Preferably, a single anomeric, enantiomeric or diastereomeric form of a compound of Formula (2) is reacted with a compound of Formula (1). Thus, if $R_2$ has a single chiral center, then the compound of Formula (2) is preferably a single enantiomer of the two possible enantiomers, or a single anomer of the two possible anomers. Furthermore, if $R_2$ has two chiral centers, then the compound of Formula (2) is preferably a single one of the possible diastereomeric forms of the compound of Formula (2). In the event that more than one anomeric, enantiomeric or diastereomeric form of $R_2$ is present in a compound of Formula (2), then preferably a single anomeric, enantiomeric or diastereomeric form is present in excess over the other anomeric, enantiomeric or diastereomeric form(s), where the excess is preferably at least about 75% anomeric, enantiomeric or diastereomeric excess, more preferably at least about 90% anomeric, enantiomeric or diastereomeric excess, and still more preferably at least about 98% anomeric, enantiomeric or diastereomeric excess. During the reaction to transfer the $R_2$ moiety to the compound of Formula (1), the anomeric, enantiomeric or diastereomeric integrity of $R_2$ is retained. For convenience, the term "diastereomeric" may be used herein to refer to any of anomeric, enantiomeric or diastereomeric.

The process of the invention thus provides for the preparation of compounds of Formula (3).

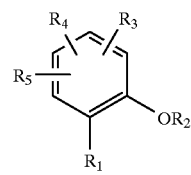

Formula (3)

wherein $R_1$, $R_2$, $R_3$, $R_4$, and $R_5$ are as defined hereinabove. It is to be noted that it is preferred that the compounds of Formula (3) do not have $R_1$ equal to bromo and $R_4$ equal to methyl when $R_2$ is (isopinocamphyloxy)methyl. Thus, in the process described above, when the compound of Formula (1) has $R_1$ equal to bromo and $R_4$ equal to methyl, then the compound of Formula (2) does not have $R_2$ equal to (isopinocamphyloxy)methyl.

Highly preferred compounds of Formula (3) are those wherein each of $R_3$, $R_4$, and $R_5$ are independently selected from the group consisting of hydrogen, protected hydroxyl, $C_{1-5}$alkyl and $C_{1-5}$alkoxy, and wherein $R_2$ is a halide of the carbohydrate or derivative thereof, such as 2,3:5,6-di-O-isopropylidene-α-D-mannofuranosyl chloride, 2,3:5,6-di-O-isopropylidene-β-D-mannofuranosyl chloride. Other $R_2$ moieties include (−)-isopinocamphyl chloromethyl ether, (+)-isopinocamphyl chloromethyl ether, (1R,2S,5R)-chloromethyl-(−)-menthol, (1S,2R,5S)-chloromethyl-(+)-menthol, (−)-chloromethyldicyclohexylsulfamoyl-D-isoborneol, (+)-chloromethyldicyclohexylsulfamoyl-L-isoborneol, 2-chloromethyl-4-(S)-isopropyloxazoline, 2-chloromethyl-4-(R)-isopropyloxazoline, 2-chloromethyl-4-(S)-phenyloxazoline or 2-chloromethyl-4-(R)-phenyloxazoline.

Especially preferred compounds of Formula (3) are 2-bromo-5-methoxyphenyl 2,3:5,6-di-O-isopropylidene-a-D-mannofuranoside, 2-bromo-5-methoxyphenyl 2,3:5,6-di-O-isopropylidene-b-D-mannofuranoside, 2-(2,3:5,6-di-O-isopropylidene-a-D-mannofuranosyloxy)chlorobenzene, and 5-chloro-2-(2,3:5,6-di-O-isopropylidene-a-D-mannofuranosyloxy)bromobenzene.

A most preferred compound of Formula (3) is 2-bromo-5-methoxyphenyl 2,3:5,6-di-O-isopropylidene-a-D-mannofuranoside, depicted in Formula (3A). The β-mannofuranoside diastereomer (not shown) of the methoxybromobenezene of Formula (3A) is also a preferred compound of Formula (3) according to the invention.

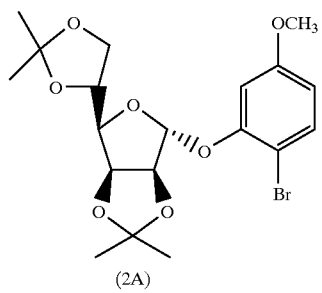

(3A)

(2A)

Another aspect of the invention is the conversion of a compound of Formula (3) into a reactive organometallic intermediate, followed by reaction of the intermediate with a cyclopentenone of Formula (4) to form a composition comprising diastereomerically-related compounds (5A) and (5B) having Formulae (5A) and (5B), respectively, as set forth in Scheme 1.

The compound of Formula (4) has the structure shown below:

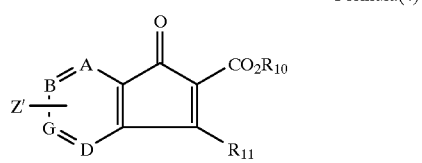

Formula (4)

In Formula (4), A, B, G, D, Z and $R_{11}$ are as defined hereinabove. $R_{10}$, as defined herein, is $C_1$–$C_5$ alkyl; however the exact identity of $R_{10}$ during the formation of the composition of compounds (5A) and (5B) is not particularly critical because it can be readily changed at any time by transesterification or functional group manipulation using techniques known to one of ordinary skill in the art. $R_{10}$ is most preferably methyl.

Compounds of Formula (4) are known in the chemical literature, and variations thereof may be prepared by simple variations on the chemistry already set forth in the literature, using knowledge available to one of ordinary skill in the art. PCT publication number WO/9308799-A1, published May 13, 1993, discloses exemplary and preferred chemistry for the preparation of compounds of Formula (4). The entire disclosure of WO/9308799 is incorporated herein by reference. A preferred compound of this disclosure is methyl 3-(3,4-methylenedioxyphenyl)-6-(prop-1-yloxy)-1-oxo-indene-2-carboxylate.

Compounds (5A) and (5B) may be prepared via a process that begins with the conversion of a compound of Formula (3) into a reactive organometallic intermediate. Formation of the reactive organometallic intermediate is achieved through conversion of the carbon atom to which the $R_1$ halogen atom is attached, into a nucleophilic center, i.e., the organometallic intermediate is prepared by halogen metal exchange from a compound of Formula (3). Methods to accomplish halogen metal exchange with an aryl halide to form an aryl reactive organometallic intermediate are known in the art, and include, e.g., reaction of an aryl halide with an alkyl lithium reagent such as butyl lithium.

The initially formed reactive organometallic intermediate may be subjected to one or more transmetallation reactions. For example, after halogen metal exchange of a compound of Formula (3) with an alkyl lithium reagent, the so-formed reactive organometallic intermediate may be treated with a second metal-containing reagent, such as a magnesium compound, e.g., magnesium bromide, to effect transmetallation and thus form an organomagnesium intermediate from the initially formed organolithium intermediate. As used herein, a reactive organometallic intermediate is the result of halogen metal exchange, optionally followed by one or more transmetallation reactions or a result of direct treatment of compound of Formula (3) with a metal.

According to a preferred process for forming a composition comprising compounds (5A) and (5B), a solution is formed by dissolving a compound of Formula (3) in a suitable solvent, where exemplary suitable solvents are inert and include THF, toluene, heptane, and the like. A suitable concentration of the compound of Formula (3) in the solvent is in the range of about 0.2 to about 0.7 molar, and is more preferably about 0.3 molar. To the solution may also be added one or more additives such as of N,N,N',N'-tetramethylethylenediamine (TMEDA) and N,N'-dimethylpropyleneurea (DMPU), and the like which are useful chelating agents for halogen metal exchange reactions with alkyl lithiums, as recognized in the art. The solution of Formula (3) compound is cooled to less than about 0° C., preferably less than about −70° C. The cooled solution of Formula (3) compound is treated with about one equivalent of an alkyl lithium reagent, such as n-BuLi. The alkyl lithium reagent is preferably predissolved in a suitable solvent or combination of solvents, for example, one or more of tetrahydrofuran, toluene and heptane, and the like. Other alkyl lithium reagents, such as sec-butyl lithium and t-butyl lithium, may alternatively be employed in the process.

After halogen metal exchange is complete or substantially complete, dry magnesium halide, e.g., $MgBr_2.Et_2O$, added to effect transmetallation, and the reaction mixture allowed to warm to about room temperature for sufficient time, e.g., a couple hours, to ensure complete formation of an organomagnesium intermediate commonly referred to as a Grignard species. A slight molar excess of the dry magnesium halide, e.g., $MgBr_2.Et_2O$, compared to the moles of compound of Formula (3) utilized in the process, is employed to ensure complete conversion of the organolithium intermediate to the organomagnesium intermediate (Grignard species). Alternatively, a compound of Formula (3) may be treated with magnesium metal (turnings or powder) at sufficient temperatures, such as between about 0° C., and 50° C., in a suitable solvent, as described above, to form the same Grignard species directly.

After ensuring formation of the organomagnesium intermediate (Grignard species), and cooling the Grignard species down to less than about −70° C., a THF solution of a cyclopentenone of Formula (4) is slowly added to the solution, while maintaining the low temperature. The cyclopentenone may be predissolved in a suitable solvent such as THF. After a couple hours, the reaction mixture is quenched with a proton source, and then allowed to come to room temperature. Workup is conveniently accomplished by, for example, washing the organic solution with aqueous brine or deionized water.

The invention thus provides for a composition comprising compounds (5A) and (5B) having Formulas (5A) and (5B) respectively, in a (5A):(5B) molar present ratio of from 100:0 to 0:100. The compounds (5A) and (5B) have the structures shown below, and are in a diastereomeric relationship to one another, according to terminology commonly used by one of ordinary skill in the art:

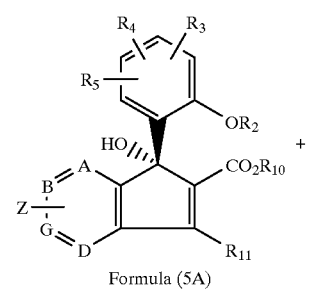

Formula (5A)

-continued

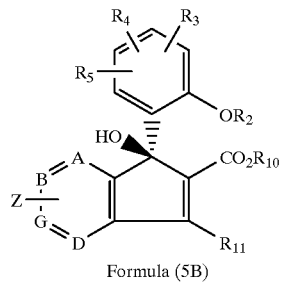

Formula (5B)

In the Formulae (5A) and (5B), the moieties $R_2$, $R_3$, $R_4$, $R_5$, A, B, G, D, Z, $R_{10}$ and $R_{11}$ are as defined hereinabove. Preferred moieties in compounds of Formulae (3) and (4) are also preferred moieties in compounds of Formulas (5A) and (5B).

As indicated hereinabove, $R_2$ is selected from the group consisting of anomers, enantiomers and diastereomers of (1) carbohydrates and derivatives thereof (2) terpenes and derivatives thereof and (3) amino acids and derivatives, thereof. The use of these $R_2$ groups is one of the keys to the present inventions and is one of the reasons why the present synthesis accomplishes the objectives described hereinabove. As shown hereinabove and described in more detail hereinbelow, the compound of Formula 3 containing $R_2$ is converted to a Grignard reagent. The $R_2$ group not only imparts chirality to the Grignard, but when it reacts with the ketone of Formula 4, the resulting product is not only stable, but the presence of the $R_2$ groups promotes the crystallization of 5A (or 5B) described hereinbelow so as to permit easy separation of the diastereomers, thereby avoiding the necessity of utlizing chromatography for separating the diastereomers. This technique which was not realized heretofore, has been successfully exploited in the present invention, as described hereinbelow.

Moreover, due to the influence of the chiral moiety $R_2$, the addition of the reactive organometallic intermediate derived from the compound of Formula (3), to the cyclopentenone of Formula (4), proceeds with high diastereoselectivity. That is, depending on the identity of $R_2$, a compound of either Formula (5A) or (5B) will be formed as the major component of a diastereomeric mixture of compounds having these Formulae. Thus, preferably, the (5A):(5B) molar percent ratio excludes 50:50, so that one of the diastereomerically-related compounds (5A) and (5B) is present in excess, and the compound in excess is denoted as the predominant isomer and the compound not in excess is denoted as the minor isomer. More preferably, the molar percent ratio of the predominant isomer to the minor isomer is 100:0 to about 75:25, still more preferably the molar percent ratio of the predominant isomer to the minor isomer is 100:0 to about 85:15, yet still more preferably the molar percent ratio is from 100:0 to about 95:5, and most preferably the molar percent ratio is from 100:0 to about 99:1. It is preferred that 5A is the predominant isomer.

As used herein, the term "molar percent ratio", such as used for example in the term "(5A):(5B) molar percent ratio of from 100:0 to 0:100", and when referring to any other pair of compounds in this specification, means that the total moles of the first listed compound, in this case (5A), divided by the total moles of both listed compounds, in this case (5A)+(5B), multiplied by 100, appears before the colon of the molar percent ratio, while the total moles of the second listed compound, in this case (5B), divided by the total moles of both listed compounds, in this case (5A)+(5B), multiplied by 100, appears after the colon. Thus, the sum of the numbers on either side of the colon in a molar percent ratio as used herein will always equal 100. When a range is stated, as in 100:0 to 0:100, this means that the stated composition includes compositions having 100% of the first listed compound and none of the second listed compound, none of the first listed compound and 100% of the second listed compound, and all ratios in between such as 60:40, 50:50 and 40:60, to name a few. The expressions "100:0 to 0:100" and "(100-0):(0-100)" are synonymous.

A most preferred composition of compounds (5A) and (5B) is a mixture of (R) and (S)-methyl-3-(3,4-methylenedioxyphenyl)-1-hydroxy-1-[2-(2,3:5,6 -di-O-isopropylidene-a-D-mannofuranosyloxy-4-methoxyphenyl]-6-propoxy-1H-indene-2-carboxylate.

Another most preferred composition of compounds (5A) and 5(B) is a mixture of (R) and (S)-5-Methyl-5-(1,3-benzodioxol-5-yl)-7-[2-(2,3:5,6-di-O-isopropylidene)-α-D-mannofuranosyloxy-4-methoxyphenyl]-7-hydroxy-7H-1-pyrindine-6-carboxylate.

According to another aspect of the invention, a composition comprising compounds of Formulas (5A) and (5B) may be subjected to one or more purification protocols in order to obtain either of the compounds (5A) or (5B) in essentially pure form. The composition of compounds of Formulas (5A) and (5B) is preferably obtained according to the previously described process starting with compounds of Formulas (3) and (4) so that one of the compounds (5A) or (5B) is the predominant isomer. The predominant isomer is preferably purified and isolated by crystallization.

According to a preferred crystallization process of the invention, the composition of compounds (5A) and (5B) is combined with one or more solvents to provide a homogeneous solution or emulsion at a first temperature. The solvent may be a pure or substantially pure solvent, such as n-butanol or isopropanol, or a mixture of solvents where exemplary solvents include ethyl acetate, hexane, n-butanol, isopropanol and water. Preferred mixtures are water with n-butanol or isopropanol, and ethyl acetate with hexane. More preferred mixtures are n-Butanol with up to 20% water and isopropanol with up to 20% water. It is most preferred that the solvent is n-Butanol. The combination of solvent and composition comprising compounds of Formulae (5A) and (5B) is then cooled to a second temperature, and if a seed of the predominant isomer is available, such a seed is added to the combination. During such a crystallization process, the mixture is preferably stirred, and the predominant isomer will gradually crystallize out of solution. A stirring time of about 20–48 hours is typical. After filtration of the crystal/mother liquor combination, crystals are isolated which contain greater than about 90% by weight of the predominant isomer, preferably greater than about 95%, and more preferably greater than about 98% by weight of the predominant isomer.

The first temperature is at least high enough to achieve complete dissolution of the compounds of Formulae (5A) and (5B) in the selected solvent or solvent pair used for the crystallization. A suitable first temperature is about 50–60° C. The second temperature is necessarily lower than the first temperature, and may be as low as room temperature or even 0° C. or lower with the preferred temperature being in the range 0 to 25° C.

The composition of compounds of Formulae (5A) and (5B) that may be subjected to the above crystallization process are all of the compositions encompassed within the description of the compounds (5A) and (5B) set forth previously. Preferred compositions of compounds of Formulae (5A) and (5B) for the crystallization process are the preferred compositions of compounds of Formulae (5A) and (5B) set forth previously.

The compound (R)-methyl-3-(3,4-methylenedioxyphenyl)-1-hydroxy-1-[2-(2,3:5,6-di-O-isopropylidene-a-D-mannofuranosyloxy-4-methoxyphenyl]-6-propoxy-1H-indene-2-carboxylate can be isolated in essentially pure form (greater than 98% diastereomeric excess) from mixtures ranging from 65:35 or greater of (R)-:(S)- methyl-3-(3,4-methylenedioxyphenyl-1-hydroxy-1-[2-(2,3:5,6-di-O-isopropylidene-a-D-mannofuranosyloxy-4-methoxyphenyl]-6-propoxy-1H-indene-2-carboxylate, using the crystallization process according to the invention.

The minor isomer may also be isolated by techniques known to the skilled artisan. The minor isomer is isolated from the mixture after the isolation of the major isomer. A preferred protocol for isolation of the minor isomer uses silica gel column chromatography. A preferred solvent for use in the chromatographic method is a combination of ethyl acetate and hexanes.

Another aspect of the invention is the stereoselective hydrogenation of a composition comprising compounds (5A) and (5B), which are preferably a diastereomeric pair, in a (5A):(5B) molar percent ratio of from 100:0 to 0:100, to afford a composition comprising compounds (6A) and (6B), which are preferably a diastereomeric pair, in a (6A):(6B) molar percent ratio of from 100:0 to 0:100.

The compounds (6A) and (6B) have the Formulae (6A) and (6B) respectively, as shown below.

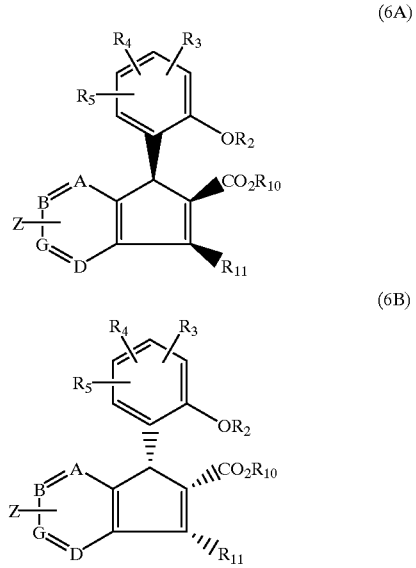

In the compounds of Formulae (6A) and (6B), $R_2$, $R_3$, $R_4$, $R_5$, A, B, D, G, Z, $R_{10}$ and $R_{11}$ are as defined hereinabove.

A preferred composition comprising compounds (6A) and (6B), which may be formed by the hydrogenation chemistry of Scheme 2, is where the compound (6A) is methyl-(1S,2S,3S)-1-(3,4-methylenedioxyphenyl)-3-[2-(2,3:5,6-di-O-isopropylidene-α-D-mannofuranosyloxy)-4-methoxyphenyl]-5-propoxyindane-2-carboxylate and the compound (6B) is methyl-(1R, 2R, 3R)-1-(3,4-methylenedioxyphenyl)-3-[2-(2,3:5,6-di-O-isopropylidene-α-D-mannofuranosyloxy)-4-methoxyphenyl]-5-propoxyindane-2-carboxylate. In this preferred composition, the (6A):(6B) molar percent ratio is preferably about (100-95):(0-5), or is about (0-5):(100-95).

The hydrogenation reaction of the invention, as shown in Scheme 2, stereoselectively hydrogenates a composition comprising diastereomerically-related compounds of Formulae (5A) and (5B). Pure or substantially pure hydrogen gas is preferably used in the hydrogenation reaction. In another embodiment a mixture of hydrogen gas and one or more inert gases is employed. Nitrogen and argon are suitable inert gases that can be mixed with hydrogen gas, where an equal molar mixture of hydrogen and nitrogen gases may be employed.

The hydrogen gas or mixture thereof is preferably contacted with compounds of Formulae (5A) and (5B) under a pressure and temperature sufficient to transform 5A to 6A or 5B to 6B. Preferably the pressure utilized is greater than atmospheric pressure, where a suitable pressure is within the range of about 10 psi to about 400 psi, preferably about 50 psi to about 200 psi, and more preferably about 80 psi to about 110 psi. The temperature at which the hydrogen gas and compounds of Formulas (5A) and (5B) are contacted may vary over a wide range, but the reaction is conducted at a temperature (and pressure) effective in producing the compounds of Formula 6A from 5A (or 6B from 5B). A preferred temperature is within the range of about 10° C. to about 60° C., where a more preferred range is about 15° C. to about 50° C. and a most preferred range is about 20° C. to about 30° C.

The compounds of Formulae (5A) and (5B) are preferably dissolved in an inert solvent prior to being contacted with hydrogen gas, where exemplary suitable solvents include $C_1-C_5$ alcohols and $C_1-C_5$ alkyl acetates, and the like. Preferred exemplary solvents are ethyl acetate, methanol and ethanol and the like. Ethyl acetate is particularly preferred. A suitable concentration of compounds of Formulae (5A) and (5B) in the solvent is about 0.01 molar to about 0.3 molar, preferably about 0.1 molar to about 0.2 molar, and more preferably about 0.1 molar to about 0.15 molar which corresponds to about 100 g of compounds of Formulae (5A) and (5B) in one (1) liter of solvent.

The hydrogenation reaction is preferably conducted in the presence of a hydrogenation catalyst, where suitable hydrogenation catalysts are commercially available and well known in the art. Exemplary hydrogenation catalysts include, without limitation, platinum oxide, palladium on alumina, palladium hydroxide on carbon and palladium on carbon. Preferably, the catalyst is palladium on alumina, palladium hydroxide on carbon or palladium on carbon, where palladium on carbon is a more preferred catalyst. The amount of metal, e.g., palladium or platinum, on a support, e.g., carbon or alumina, can vary over a wide range. For example, catalysts having from about 1% to about 20% palladium on carbon are known and may be used in the invention. A preferred palladium on carbon (Pd/C) catalyst has about 5% to about 15% palladium on carbon, and more preferably has about 10% to about 15% palladium on carbon. There are several different types of carbon that may be used as the support, e.g., charcoal, and the like.

Palladium on carbon catalysts are well known in the art, and may be obtained from many commercial supply houses, e.g., Aldrich Chemical Company (Milwaukee, Wis.) or Precious Metal Corp. (Sevierville, Tenn.) as their product Type # 1910 having 15% palladium on carbon, where the number 1910 indicates a specific type of carbon.

Hydrogenation catalysts may be basic, neutral or acidic. Typically, supply houses do not specify the acidity of the catalyst, as this parameter is not often of importance in hydrogenation reactions. Indeed, the same supplier may provide two batches of catalyst where one batch may be acidic and the other batch may be basic. However, in order to achieve high stereoselectivity in the hydrogenation of a composition comprising compounds of Formulae (5A) and (5B), it has been discovered that the pH of the catalyst is a very important processing factor. Thus, if an acidic catalyst is employed in the hydrogenation reaction, the stereoselectivity of the reaction is reduced compared to a reaction run in the presence of a slightly basic or neutral catalyst. Therefore, the hydrogenation catalyst preferably has a pH of greater than about 6, more preferably has a pH between about 6.5 and about 8, and still more preferably has a pH of about 6.8 to about 7.5. It is thus preferred that the Pd/C hydrogenation catalyst be neutral or slightly basic. Precious Metal Corp. will provide their Type # 1910 15% palladium on carbon as essentially a neutral catalyst, 50% water wet, and this catalyst is preferred for the hydrogenation reaction of the invention. Commercially available acidic catalysts may be used if washed sufficiently with water at about neutral pH to thereby provide a neutral catalyst.

The hydrogenation reaction of Scheme 2 is preferably conducted with agitation. That is, a stirrer is preferably present in the reaction vessel, to provide for stirring of the mixture of catalyst, solvent and compounds of Formulae (5A) and/or (5B). In this way, the surface of the catalyst comes into periodic contact with the hydrogen atmosphere. The progress of the reaction may be determined by periodically pulling samples and analyzing those samples by an appropriate analytical method, e.g., by HPLC. The uptake of hydrogen may also be monitored, and compared to the theoretical uptake, in order to gauge the progress of the hydrogenation reaction. In general, when the hydrogenation reaction is conducted at about ambient temperature, i.e., about 25° C., a reaction time of between about 2 to about 48 hours is usually required.

Preferably, the hydrogenation reaction proceeds with high stereoselectivity. That is, a compound of Formula (5A) is hydrogenated to form almost exclusively a compound of Formula (6A), while a compound of Formula (5B) is hydrogenated to form almost exclusively a compound of Formula (6B). The term "almost exclusively" means that at least about 90%, preferably at least about 95% and more preferably at least about 98% of the compound of Formula (5A) or (5B) will be converted to a compound of Formula (6A) or (6B), respectively. Thus, if the (5A):(5B) molar percent ratio of compounds of Formulas (5A) and (5B) in the starting material is about (100-90):(0-10) (compound of Formula (5A) in excess) or about (0-10):(100-90) (compound of Formula (5B) in excess), then the (6A):(6B) molar percent ratio of the compounds of Formulas (6A) and (6B) in the product will also be about (100-90):(0-10) (compound of Formula (6A) in excess when the starting composition had the compound of Formula (5A) in excess) or about (0-10):(100-90) (compound of Formula (6B) in excess when the starting composition had the compound of Formula (5B) in excess).

The chemistry in Scheme 2 thus illustrates the process wherein a composition comprising compounds (5A) and (5B) in a (5A):(5B) molar percent ratio of from 100:0 to 0:100 is selected and then contacted with hydrogen gas in the presence of a basic or neutral hydrogenation catalyst to achieve a hydrogenation reaction. Preferably, the hydrogenation catalyst is about 10 wt. % to about 15 wt. % palladium on carbon having a pH of about 6.8 to about 7.5, and the hydrogenation reaction is conducted in the presence of ethyl acetate as a solvent. The molar percent ratio of compounds (5A):(5B) in the starting material is substantially the same as the molar percent ratio of compounds (6A):(6B) formed as products. A preferred composition comprising compounds (5A) and (5B) is at least one of (R)- and (S)-methyl-3-(3,4-methylenedioxyphenyl)-1-hydroxy-1-[2-(2,3:5,6-di-O-isopropylidene-α-D-mannofuranosyloxy)-4-methoxyphenyl]-6-propoxy-1H-indene-2-carboxylate.

After the hydrogenation reaction is complete, the product mixture is optionally filtered to separate the hydrogenation catalyst from the solvent and dissolved materials. It is convenient to filter the reaction mixture through Celite to obtain a solubilized product mixture of compounds of Formulae (6A) and (6B). Other filter aids known in the art may also be employed.

The composition comprising compounds (6A) and (6B) is optionally subjected to further purification in order to obtain one of the compounds (6A) or (6B) in essentially pure form. A preferred purification procedure is crystallization. Using crystallization, crystals formed essentially of only a single one of the compounds (6A) or (6B) may be obtained. The isomeric purity of the crystals will depend, in part, on the identity of the solvent from which the crystals form. Absolute ethanol is a preferred solvent, because it provides for the formation of crystals having a single isomer in very high enantiomeric or diastereomeric purity. However, other solvents may also be used in the crystallization process, and will provide for crystals of enhanced isomeric purity, where the degree of purity depends in part on the specific structures of the compounds (6A) and (6B). Suitable solvents for the crystallization include, without limitation, ethanol, optionally containing about 1% to about 5% of a second solvent such as toluene, methanol or ethyl acetate, and absolute ethanol, optionally containing up to about 10% of a second solvent such as toluene, methanol or ethyl acetate. Absolute ethanol with up to about 10% ethyl acetate is a preferred crystallization solvent, while absolute ethanol without any co-solvent is more preferred.

In general, the crystallization process dissolves compounds (6A) and (6B) in a solvent at an elevated dissolution temperature, and then holds the mixture at a crystallization temperature lower than the dissolution temperature while crystals form. The precise dissolution and crystallization temperatures can vary over wide ranges, and will depend on the solubility and concentration of the compounds (6A) and (6B) in the crystallization solvent. One of ordinary skill in the art can determine these temperatures and suitable concentrations without undue experimentation. A suitable crystallization temperature is less than about 40° C., is preferably about 20° C. to about 40° C., and is more preferably about 30° C. to about 40° C.

According to a preferred purification process, the composition of compounds (6A) and (6B) is heated to reflux in order to distill off some of the solvent used in the hydrogenation reaction. Then the crystallization solvent, e.g., ethanol, is added and the resulting mixture again heated to reflux to distill off more of the hydrogenation solvent. Several chases may be necessary to replace essentially all of the hydrogenation solvent with ethanol. After a solution of the composition of compounds (6A) and (6B) in ethanol has been formed at an elevated dissolution temperature, the solution is cooled with gentle stirring. Preferably, the solution is cooled to a crystallization temperature of about 20° C. to about 40° C. In this temperature range, and after a few hours of stirring, crystals enriched in one of the compounds (6A) or (6B) will form and can be isolated by, techniques known to the skilled artisan e.g., filtration.

Preferably, after the crystallization process, a single one of the diastereomerically-related compounds (6A) and (6B) may be obtained as crystals having very high diastereomeric excess, e.g., a diastereomeric excess greater than about 75%, preferably greater than about 90%, more preferably greater than about 95% and still more preferably greater than about 98% diastereomeric excess.

The invention further provides for a compound of Formula (6A) to be converted to a compound of Formula (7A) according to the chemistry outlined in Scheme 3, Routes (A) and (B). While the chemistry outlined in Scheme 3 is illustrated starting with a compound of Formula (6A) for convenience, it should be understood that the same chemistry can be used to convert a compound of Formula (6B) to a compound of Formula (7B), and to convert a composition comprising compounds of Formulae (6A) and (6B), having a (6A):(6B) molar percent ratio of 100:0 to 0:100, to a composition comprising compounds of Formula (7A) and (7B), having a (7A):(7B) molar percent ratio of 100:0 to 0:100. As explained previously, compounds of Formulas (7A) and (7B) are useful as endothelin receptor antagonists.

Looking first at Scheme 3, Route (A), Step (1), a compound of Formula (6A) is treated with Brønsted acid. This affects cleavage of the aryl ether —OR$_2$ group in a compound of Formula (6A) and forms a phenolic —OH group in a compound of Formula (8A). The preferred acid is hydrochloric acid, which is dissolved in water at a concentration of about 5 wt. % to about 37 wt. %. Preferably, concentrated (con.) hydrochloric acid, i.e., 37 wt. % aqueous HCl, is the acid for the cleavage reaction. Other suitable Brønsted acids that may be employed include, without limitation, hydrobromic acid, phosphoric acid, hypophosphorous acid, sulfuric acid, para-toluenesulfonic acid, methanesulfonic acid and the like.

The ratio of acid to compounds of Formulae (6A) and (6B) can vary over a wide range, and will depend upon the concentration of acid being employed. When the acid is hydrochloric acid at 37 wt. % in water, a concentration of about 40 mL to about 200 mL acid for about 0.1 mol to about 1 mol of compounds of Formulas (6A) and (6B) is suitable for the cleavage reaction. Preferably, about 50 mL to about 100 mL hydrochloric acid is used for about 0.1 mol to about 1.0 mol of the compounds of Formula (6A) and (6B), where a more preferred ratio is about 70 mL to about 80 mL acid for about 0.4 to about 0.6 mol of compounds of Formulas (6A) and (6B).

The compounds of Formulae (6A) and (6B) are preferably slurried in a solvent prior to treatment with acid. Aliphatic alcohols or polyols, and aliphatic ethers and polyethers are suitable solvents. A preferred solvent is a $C_1$–$C_4$ alcohol, where methanol is a particularly preferred solvent. An elevated temperature is preferably employed in Step (1) in order to obtain a commercially desirable rate for the reaction. A reaction temperature of between about 20° C. to about the reflux temperature of the reaction mixture, although preferably not greater than about 70° C., is suitable. Preferably, a temperature of about 50° C. to about the reflux temperature is employed, while a more preferred temperature is at the reflux temperature of the reaction mixture. The reaction will be slower at lower temperatures. Preferably, methanol is used as the solvent in Step (1) and the reaction temperature is about the reflux temperature of the reaction mixture including methanol, i.e., about 60° C. to about 65° C. The progress of the reaction may be monitored by periodically pulling samples and analyzing the samples by an analytical technique, e.g., by HPLC.

An optional but preferred Step (1) includes a purification step after the formation of a compound of Formula (8A). A preferred purification step begins with the compound of Formula (8A) at about the reflux temperature of the reaction mixture that includes the compound of Formula (8A), where the compound of Formula (8A) is still in the presence of the Brønsted acid. The reaction mixture is cooled to about 20° C. to about 40° C., preferably about 30° C., and then a seed crystal of the desired product may be added. After continuous stirring for about 18 hours at about ambient temperature, the seeded slurry may be cooled to about 0° C. to about 10° C., preferably to about 0° C. to about 5° C., for an additional 2–10 hours, preferably about 4 hours, and then the resulting crystals isolated by filtration. According to this purification procedure of Step (1), crystals having at least about 90% by weight of a single enantiomer, preferably at least about 95% and more preferably at least about 99% of a single enantiomer, are formed. The crystals may have an enantiomeric excess of greater than about 99%.

As explained above, the chemistry used to convert a compound of Formula (6A) to a compound of Formula (8A) according to Step (1) may be generally used to prepare a composition comprising compounds (8A) and (8B), having an (8A):(8B) molar percent ratio of from 100:0 to 0:100, from a composition comprising compounds (6A) and (6B), having a (6A):(6B) molar percent ratio of from 100:0 to 0:100, wherein the compounds (8A) and (8B) have the Formulae (8A) and (8B), respectively.

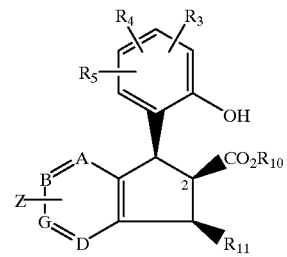

(8A)

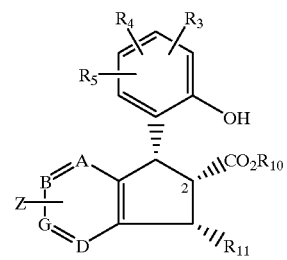

(8B)

Following Step (1) in Route (A) of Scheme 3 is Step (2), wherein a phenolic compound of Formula (8A) is alkylated to form a compound of Formula (9A). The purpose behind the sequence of Steps (1) and (2), which have the overall effect of converting —OR$_2$ to —OR$_{12}$, is that R$_2$ is particularly suited to allowing the formation of a composition comprising diastereomerically-related compounds (5A) and (5B) from compounds (3) and (4) where the composition is highly enriched in one of the two diastereomers due to the influence of R$_2$, while R$_{12}$ is particularly suited to enhancing the efficacy of a compound of Formula (7A) as an endothelin receptor antagonist.

Alkylation chemistry for phenolic compounds is well known in the art, and any such chemistry may be used for the alkylation of a compound of Formula (8A). Upon alkylation, a compound of Formula (9A) is prepared, where the group R$_{12}$ has been added to the compound of Formula (8A) to form an aryl ether.

The alkylation of Step (2) in Route (A) proceeds by contacting a compound of Formula (8A) with an alkylating agent. A preferred alkylating agent is $L_1$—$(CH_2)_pCO_2R_{13}$, where $R_{13}$ is a $C_{1-5}$ alkyl group and p is an integer from 1 to 3. In this case, $R_{12}$ will be —$(CH_2)_pCO_2R_{13}$. "$L_1$" in the alkylating agent is a leaving group, where the term "leaving group" as used herein denotes an atom or atomic arrangement that is sufficiently stable in anionic form to detach from a carbon atom in response to nucleophilic attack at that carbon by a phenolic oxygen atom. Exemplary leaving groups include chloride, bromide and iodide. Many hydroxyl derivatives, e.g., derivatives prepared by the conversion of a hydroxyl group into an ester of a relatively strong acid, are leaving groups according to the invention. Exemplary hydroxyl group derived leaving groups include, without limitation, para-toluenesulfonyl ester (tosylate group), methanesulfonyl ester (mesylate group) and alkyl esters, such as acetate ester, and the like. Chloride and bromide are preferred leaving groups "$L_1$" according to the invention, and methyl bromoacetate, i.e., $L_1$=Br, p=1 and $R_{13}$=$CH_3$, is a preferred alkylating agent for a compound of Formula (8A).

Another preferred alkylating agent is ethylene carbonate. When a compound of Formula (8A) is contacted with ethylene carbonate, preferably in the presence of base, the $R_{12}$ group in the compound of Formula (9A) is —$(CH_2)_2OH$.

The alkylation reaction is preferably conducted in the presence of base. Suitable bases include, without limitation, sodium hydride, potassium hydride, potassium carbonate and the like. The potassium carbonate may be in, e.g., powder or granular form. Other bases could also be employed, where suitable bases are known to one of ordinary skill in the art. When the alkylating agent is ethylene carbonate, the base is preferably potassium carbonate, and is more preferably anhydrous powdered potassium carbonate. About 2 to about 20 equivalents of base are suitably used per equivalent of compound of Formula (8A). Preferably, about 2 to about 8 equivalents are employed, while more preferably about 4 to about 6 equivalents of base are employed.

The alkylation reaction is also preferably conducted in a solvent, where suitable solvents include, without limitation, aromatic solvents and halogenated versions thereof such as benzene, toluene, xylenes, chlorobenzene and polychlorobenzene; and ethers such as $C_3$–$C_5$ alkyl ethers. Toluene, xylenes, chlorobenzene and polychlorinated benzenes are preferred solvents, while toluene is a particularly preferred solvent.

The reaction mixture in the alkylation reaction of Step (2) is conducted at temperatures effective to produce the desired product. Preferably, the reaction mixture in the alkylation reaction of step (2) is taken to elevated temperature, such as about 50° C. to about the reflux temperature of the reaction mixture, in order to achieve a satisfactory reaction rate. Preferably, the reaction temperature is about 100° C. to about 120° C., and when toluene is the reaction solvent, the preferred temperature is about 110° C. to about 115° C., which is the reflux temperature of the reaction mixture.

When ethylene carbonate is the alkylating agent, it is preferred that a high temperature of about 100° C. to about 120° C. is preferably employed in order to obtain a reasonable rate for the alkylation reaction. However, at these high temperatures, lactonization between the phenolic hydroxyl group and the carboxylate ester at position 2 of the indane ring, may be a significant problem due to the particular stereochemistry of the compounds of Formulae (8A) and (8B). However, it has been surprisingly discovered that extended reaction times at elevated temperatures may convert any lactone intermediate that does form into the desired alkylated product.

As explained above, the chemistry used to convert a compound of Formula (8A) to a compound of Formula (9A) according to Step 2 may be generally used to prepare a composition comprising compounds (9A) and (9B), having a (9A):(9B) molar percent ratio of from 100:0 to 0:100, from a composition comprising compounds (8A) and (8B), having an (8A):(8B) molar percent ratio of from 100:0 to 0:100, where the compounds (9A) and (9B) have the Formulae (9A) and (9B), respectively.

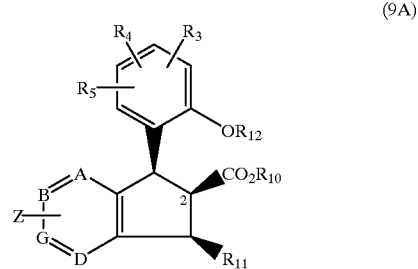

(9A)

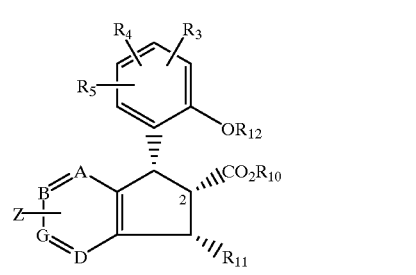

(9B)

Thus, the chemistry described above affords a composition comprising compounds (9A) and (9B) having the Formulae (9A) and (9B) respectively, in a (9A):(9B) molar percent ratio of 100:0 to 0:100, wherein $R_3$, $R_4$, $R_5$, A, B, G, D, Z, $R_{10}$, $R_{11}$ and $R_{12}$ are as defined hereinabove.

A preferred composition of the compounds (9A) and (9B) are methyl (1S, 2S, 3S)-1-(3,4-methylenedioxyphenyl)-3-[2-(2-hydroxyeth-1-yloxy)-4-methoxyphenyl]-5-propoxyindane-2-carboxylate and methyl-(1R, 2R, 3R)-1-(3,4-methylenedioxyphenyl)-3-[2-(2-hydroxyeth-1-yloxy)-4-methoxyphenyl)-5-propoxyindane-2-carboxylate, respectively, and the molar percent ratio of (9A):9(B) is about (100-95):(0-5). Such a composition may be prepared by selecting a composition comprising compounds (8A) and (8B), wherein the compounds (8A) and (8B) are methyl-(1S, 2S, 3S)-1-(3,4methylenedioxyphenyl)-3-(4-methoxy-2-hydroxyphenyl)-5-propoxyindane-2-carboxylate and methyl-(1R, 2R, 3R)-1-(3,4-methylenedioxyphenyl)-3-(4-methoxy-2-hydroxyphenyl)-5-propoxyindane-2-carboxylate, respectively, and the molar percent ratio of (8A):(8B) is about (100-95):(0-5), and then treating the composition comprising compounds (8A) and (8B) with ethylene carbonate in the presence of potassium carbonate in toluene at a temperature of about 100° C. to about 120° C.

In an embodiment of the present invention, the compound of Formula (9A) is treated with base such as hydroxides, alkoxides, and the like, in the presence of water in a suitable solvent mixture such a methanol and tetrahydrofuran to achieve saponification and epimerization of the carboxylate group at position 2 of the compound, to thereby form a compound of Formula (7A) as shown in Route (A), Step (3) of Scheme 3. Compounds of Formula (7A) are known endothelin receptor antagonists, as reported in WO/9308799 incorporated herein by reference. Specific reaction conditions saponification and epimerization reaction are generally known in the art. In addition, examples of such reaction conditions are set forth in WO/9308799, incorporated herein by reference, and will not be further described herein.

Thus, according to Route (A) of Scheme 3, a composition comprising compounds (6A) and (6A), having a (6A):(6B) molar percent ratio of from 100:0 to 0:100 may be converted to a composition comprising compounds (7A) and (7B), having a (7A):(7B) molar percent ratio of from 100:0 to 0:100.

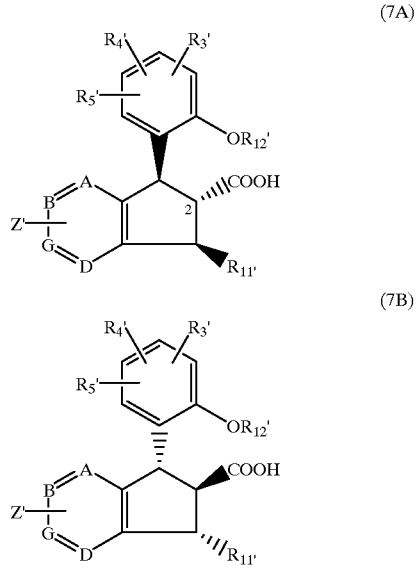

(7A)

(7B)

In the formula, $R_3'$, $R_4'$, $R_5'$, A, B, D, G, Z', $R_{11}'$ and $R_{12}'$ are as defined hereinabove.

Preferably, in the chemistry outlined above, the starting material compositions are significantly enriched in one of the diastereomerically-related compounds of Formulas (6A&B), (8A&B) or (9A&B). The term "significantly enriched" means that the starting material compositions are not racemic, i.e., they do not contain equal molar amounts of the compounds (6A) and (6B), or equal molar amounts of the compounds (8A) and (8B), or equal molar amounts of the compounds (9A) and (9B). Preferably, the molar percent ratio of any two of the above-listed diastereomerically-related compounds is about (100-75):(0-25), more preferably is about (100-90):(0-10), still more preferably is about (100-95):(0-5), and yet still more preferably is about (100-98):(0-2), where either of the diastereomerically-related compounds (6A)/(6B), (8A)/(8B) or (9A)/(9B) may be in excess of the other.

According to another aspect of the invention, the conversion of a compound of Formula (6A) to a compound of Formula (7A) may proceed through Route (B) as identified in Scheme 3, where the intermediates formed in the conversion according to Route (B) are more completely shown in Scheme 4.

As illustrated by Step (4A) in Scheme 4, a compound of Formula (6A) may be converted to a compound of Formula (10A) by epimerization of the carboxylate ester at position 2. The epimerization reaction is preferably accomplished by treating a compound of Formula (6A) with base in the presence of solvent at an elevated temperature. Suitable bases for the reaction of Step (4A) include alkali metal hydroxides, such as lithium hydroxide, sodium hydroxide and potassium hydroxide, as well as alkali metal alkoxides, such as sodium ethoxide and sodium methoxide. Alkali metal hydroxides are preferred, with lithium hydroxide being a particularly preferred base for the epimerization reaction.

Suitable solvents for the reaction of Step (4A) include water, lower alkyl (e.g., $C_1$–$C_5$) ethers and lower alkyl alcohols and polyols, as well as mixtures thereof Water, tetrahydrofuran, methanol, ethanol and propanol are exemplary solvents, with methanol and tetrahydrofuran in combination with water being a preferred solvent. A suitable reaction temperature is about 20° C. to about the reflux temperature of the reaction mixture, preferably about 50° C. to the reflux temperature of the reaction mixture, and more preferably about the reflux temperature of the reaction mixture.

As explained above, the chemistry used to convert a compound of Formula (6A) to a compound of Formula (10A) according to Step (4A) may be generally used to prepare a composition comprising compounds (10A) and (10B), having a (10A):(10B) molar percent ratio of from 100:0 to 0:100, from a composition comprising compounds (6A) and (6B), having a (6A):(6B) molar percent ratio of from 100:0 to 0:100, wherein the compounds (10A) and (10B) have the Formulae (10A) and (10B), respectively.

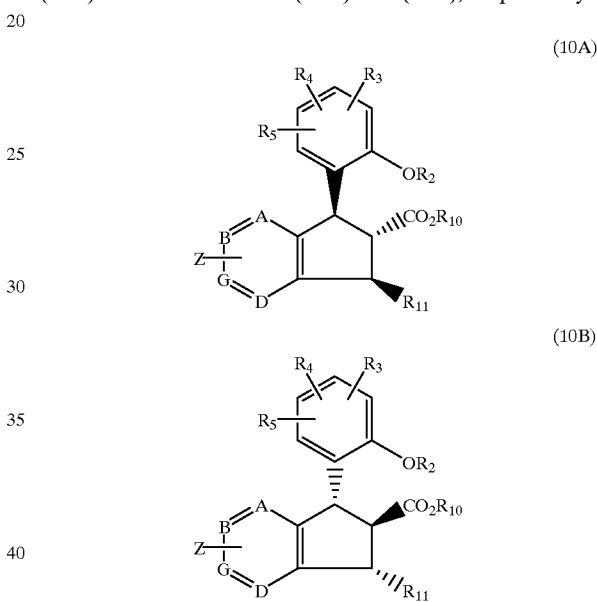

(10A)

(10B)

In formulae 10A and 10B, $R_3$, $R_4$, $R_5$, $R_2$, A, B, D, G, Z, $R_{11}$ and $R_{10}$ are as defined hereinabove.

The basic conditions that cause the epimerization reaction for converting a compound of Formula (6A) to a compound of Formula (10A) according to Step (4A), may subsequently cause hydrolysis of the ester compound of Formula (10A) to form the carboxylate compound of Formula (11A) according to Step (4B). However, in order for the hydrolysis reaction to proceed immediately after the epimerization reaction, some water must be present in the reaction mixture. Thus, in an aqueous solvent, preferably containing some lower alcohol, the basic conditions used in Step (4A) may cause not only the epimerization of the carboxylate ester at position 2, but also the hydrolysis of the carboxylate ester at position 2 to form a carboxylic acid as shown in Formula (11A). If water is not present in the solvent used to convert a compound of Formula (6A) to a compound of Formula (10A), then water should be added to a compound of Formula (10A) in order achieve its hydrolysis and the subsequent formation of a compound of Formula (11A).

As explained above, the chemistry used to convert a compound of Formula (10A) to a compound of Formula (11A) according to Step (4B) may be generally used to prepare a composition comprising compounds (11A) and (11B), having an (11A):(11B) molar percent ratio of from 100:0 to 0:100, from a composition comprising compounds (10A) and (10B), having a (10A):(10B) molar percent ratio of from 100:0 to 0:100, wherein the compounds (11A) and (11B) have the Formulae (11A) and (11B), respectively. In addition, under aqueous reaction conditions, a composition comprising compounds (6A) and (6B) and having a (6A):(6B) molar percent ratio of from 100:0 to 0:100 may be converted to a composition comprising compounds (11A) and (11B), having an (11A):(11B) molar percent ratio of from 100:0 to 0:100, without need to isolate or purify the intermediate compounds (10A) or (10B).

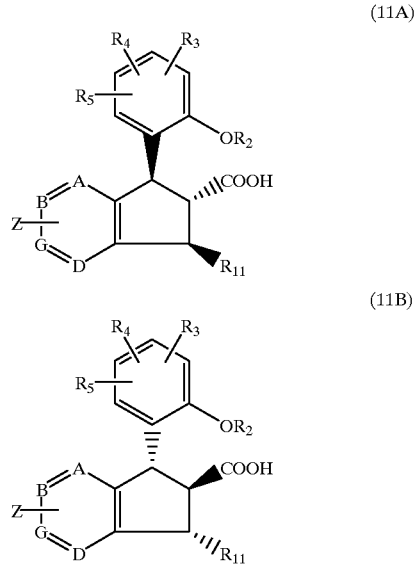

In formulae 11A and 11B, $R_2$, $R_3$, $R_4$, $R_5$, A, B, D, G, Z and $R_{11}$ are as defined hereinabove.

The invention also provides for the conversion of a compound of Formula (11A) to a compound of Formulas (12A), and the subsequent conversion of a compound of Formula (12A) to a compound of Formula (13A). It is not necessary to isolate the compound of Formula (12A). Indeed, a compound of Formula (11A) is preferably reacted under conditions that immediately convert a compound of Formula (12A) to a compound of Formula (13A) so that a compound of Formula (12A) is not isolated. Furthermore, it is preferred to carry out the conversion of a compound of Formula (6A) to a compound of Formula (13A) in a single reaction kettle, without isolation of any of the intermediate compounds (10A), (11A) or (12A). While either of compounds of Formula (11A) or (12A) could be isolated and purified, these isolation steps are not preferred because they increase the expense of preparing the endothelin receptor antagonists of interest.

Thus, according to a preferred process, the product mixture containing a compound of Formula (11A) as prepared according to Step (4B), which also contains water and base, is extracted with an organic hydrophobic solvent. Suitable organic hydrophobic solvents include aliphatic and aromatic hydrocarbons and chlorohydrocarbons, and the like. The preferred organic hydrophobic solvent, preferably has a boiling point of less than about 150° C. Xylenes, toluene and chlorobenzene are preferred solvents for the extraction step, with toluene being particularly preferred.

Alcohol is a preferred solvent for Step (5B), and alcohol is also a suitable solvent for Step (5A). Thus, the invention provides for the organic hydrophobic solvent to be replaced with an alcohol solvent. Suitable alcohol solvents have the Formula HO—$R_{13}$, wherein $R_{13}$ is $C_{1-5}$alkyl. Suitable solvents include methanol, ethanol, n-propanol and isopropanol. The alcohol solvent is preferably a primary alcohol, and is more preferably methanol or ethanol.

In order to replace toluene, or whatever organic hydrophobic solvent has been used for the extraction of Step (5A), with an alcohol solvent, the solution of the compound of Formula (11A) in an organic hydrophobic solvent is concentrated using distillation, and the compound of Formula (11A) redissolved in alcohol. A preferred alcohol solvent is methanol, i.e., $R_{13}$ is methyl. Some Brønsted acid is added to the alcohol solution of the compound of Formula (11A) in order to effect cleavage of the aryl ether —$OR_2$ group, according to Step (5A). Suitable and preferred Brønsted acids are the same as those set forth above in connection with Scheme 3, Route (A), Step (1). Also, the suitable and preferred temperatures at which the compound of Formula (11A) is converted to a compound of Formula (12A) are the same as the suitable and preferred temperature set forth in connection with Scheme 3, Route (A), Step (1).

The preferred concentration of acid used in Step (5A), and optionally Step (5B), is about 20 mL to about 200 mL per about 0.05 to about 1.0 mol of the aryl ether compound of Formula (11A). Preferably, the ratio of acid to the aryl ether compound of Formula (11A) is about 30 mL to about 100 mL acid per 0.1 to about 0.5 mol of aryl ether, and more preferably is about 40 mL to about 60 mL acid per 0.1 to about 0.15 mol aryl ether.

In order to convert the compound of Formula (12A) to a compound of Formula (13A), the reaction mixture from Step (5A) is taken to a sufficient temperature to effect the conversion. Preferably, the temperature ranges from about 20° C. to about 80° C., more preferably about 40° C. to about 80° C., and most preferably about 50° C. to about 70° C. It is typically the case that Step (5B) should be conducted at a higher temperature than is necessary for Step (5A), in order to achieve a commercially desirable rate for the conversion of a compound of Formula (11A) to a compound of Formula (13A).

As explained above, the chemistry of Step (5A), used to convert a compound of Formula (11A) to a compound of Formula (12A), can also generally be used to prepare a composition comprising compounds (12A) and (12B), having a (12A):(12B) molar percent ratio of from 100:0 to 0:100, from a composition comprising compounds (11A) and (11B), having an (11A):(11B) molar percent ratio of from 100:0 to 0:100, wherein the compounds (12A) and (12B) have the Formulae (12A) and (12B), respectively.

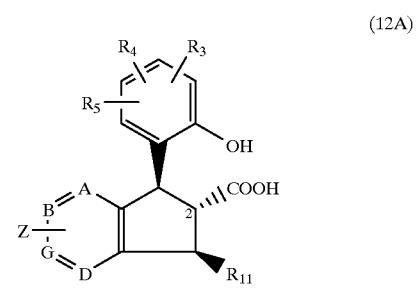

-continued

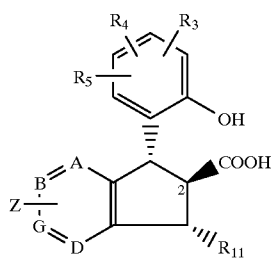

(12B)

In formulae 12A and 12B, $R_3$, $R_4$, $R_5$, A, B, G, D, Z and $R_{11}$ are as defined hereinabove.

The composition of compounds having Formulae (12A) or (12B) is converted to a composition of compounds having the Formulae (13A) or (13B), respectively. Furthermore, under the reaction conditions described in accordance with Scheme 4, the compounds of Formulae (11A) and (11B) can be converted directly to compounds of Formulas (13A) and (13B), without the isolation or purification of any (12A) or (12B) compounds. The compounds (13A) and (13B) have the Formulae (13A) and (13B), respectively.

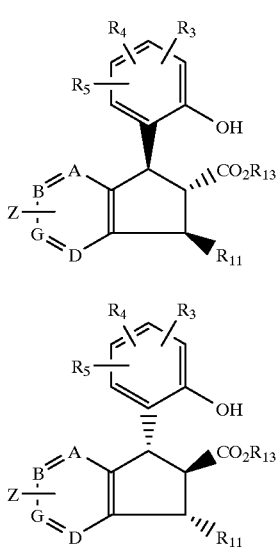

(13A)

(13B)

In Formulae 13A and 13B, $R_3$, $R_4$, $R_5$, A, B, G, D, Z, $R_{11}$, and $R_{13}$ are as defined hereinabove.

It is preferred to conduct Steps 4A, 4B, 5A and 5B (as outlined in Scheme 4), in a single reaction flask, without having isolated or purified any of the compounds of Formulae (10A), (11A) or (12A) by distillation, chromatography or the like. This can be accomplished by treating a compound of Formula (6A) with base and water in a suitable solvent to provide a compound of Formula (11A), then neutralizing the base with acid and treating the compound of Formula (11A) with acid in the presence of an alcohol solvent. Thus, according to the chemistry detailed above, and without any intermediate purification steps, a composition comprising compounds (6A) and (6B), having a (6A):(6B) molar percent ratio of from 100:0 to 0:100, can be converted to a composition comprising compounds (13A) and (13B), having a (13A):(13B) molar percent ratio of from 100:0 to 0:100.

With the compound of Formula (13A) in hand, Step (6) is an alkylation reaction of the phenolic —OH group formed in Step (5A). Thus, in Step (6), the compound of Formula (13A) is treated with an alkylating agent in the presence of a base. The reaction conditions for Step (6) are essentially the same as the reaction conditions that were described above in connection with Step (2), which was also an alkylation reaction of a phenolic compound. Preferred alkylating agents are ethylene carbonate and methyl bromoacetate.

Alkylation of a compound of Formula (13A) affords an aryl ether of Formula (14A). Thus, as explained above, the alkylation chemistry used to convert a compound of Formula (13A) to a compound of Formula (14A) according to Step (6) may be generally used to prepare a composition comprising compounds (14A) and (14B), having an (14A):(14B) molar percent ratio of from 100:0 to 0:100, from a composition comprising compounds (13A) and (13B), having a (13A):(13B) molar percent ratio of from 100:0 to 0:100, wherein the compounds (14A) and (14B) have the Formulae (14A) and (14B), respectively.

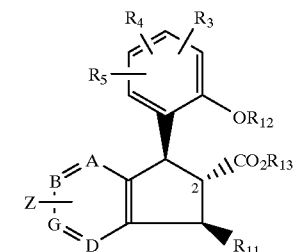

(14A)

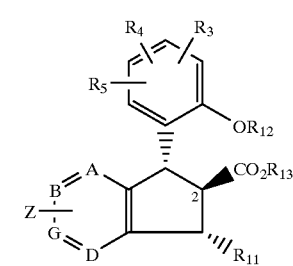

(14B)

In Formulae 14A and 14B, $R_3$, $R_4$, $R_5$, $R_6$, $R_{11}$, $R_{12}$, $R_{13}$, A, B, D, G and Z are as defined hereinabove.

The invention thus provides a one-pot process for preparing a composition comprising compounds (14A) and (14B) with a (14A):(14B) molar percent ratio of 100:0 to 0:100. The preferred one-pot process selects a composition comprising compounds (6A) and (6B) with a (6A):(6B) molar percent ratio of 100:0 to 0:100; wherein the compounds (6A), (6B), (14A) and (14B) have the Formulae (6A), (6B), (14A) and (14B), as set forth above. The selected composition is then treated with base to afford epimerization of the carboxylate ester at position 2. The thus formed epimerized product is treated with aqueous base to saponify the carboxylate ester at position 2 and afford a carboxylic acid or salt. The thus saponified product is then treated with acid to achieve cleavage of the —$OR_2$ group and thereby afford a compound with a phenolic —OH group. The thus formed phenolic compound is treated with a $C_{1-5}$monohydric compound of Formula $R_{13}$—OH, in the presence of acid to afford esterification of the carboxylic acid group at position 2. Finally, the thus formed esterified product is treated with base and an alkylating agent to afford a composition comprising compounds (14A) and (14B).

According to a more preferred one-pot process for preparing compounds of Formulae (14A) and (14B), the selected composition according to the previous paragraph is treated with lithium hydroxide in the presence of tetrahydrofuran, methanol and water to afford an epimerized and saponified product of Formulae (11A&B), which is then treated with hydrochloric acid and methanol to afford an esterified phenolic compound of Formulae (13A&B), which is then treated with potassium carbonate and an alkylating agent such as ethylene carbonate or L—$(CH_2)_pCO_2R_{13}$, to afford a composition comprising compounds (14A&B).

According to a still more preferred one-pot process for preparing compounds of Formulae (14A) and (14B), the selected composition comprises the compound (6A) which is methyl-(1S, 2S, 3S)-1-(3,4-methylenedioxyphenyl)-3-[2-(2,3:5,6-di-O-isopropylidene-α-D-mannofuranosyloxy)-4-methoxyphenyl]-5-propoxyindane-2-carboxylate and compound (6B) which is methyl-(1R, 2R, 3R)-1-(3,4-methylenedioxyphenyl)-3-[2-(2,3:5,6-di-O-isopropylidene-α-D-mannofuranosyloxy)-4-methoxyphenyl]-5-propoxyindane-2-carboxylate, and the (6A):(6B) molar percent ratio is preferably about (100-95):(0-5) or about (0-5):(100-95).

In an embodiment of the present invention, the compound of Formula (14A) is saponified according to Step 7 to provide an endothelin receptor antagonist of Formula (7A). The saponification of Step 7 is analogous to the saponification of Step 3 in Route (A), and thus will not be discussed in detail. As explained above, the chemistry used to convert a compound of Formula (14A) to a compound of Formula (7A) according to Step 7 may be generally used to prepare a composition comprising compounds (7A) and (7B), having a (7A):(7B) molar percent ratio of from 100:0 to 0:100, from a composition comprising compounds (14A) and (14B), having a (14A):(14B) molar percent ratio of from 100:0 to 0:100.

Preferably, in the chemistry outlined above for Route (B), the starting material compositions are significantly enriched in one of the diastereomerically-related compounds of Formulae (6A&B), (10A&B), (11A&B), (12A&B), (13A&B) or (14A&B). The term "significantly enriched" has the same meaning as set forth above in connection with the compounds formed and used in Route (A).

According to Route B, and as explained above, the invention provides for compounds of Formulae (10A&B), (11A&B), (12A&B), (13A&B) and (14A&B), where compounds of Formulae (14A&B) may be converted to endothelin receptor antagonists of Formulae (7A&B). The invention thus provides for compositions comprising diastereomerically-related compounds (15A) and (15B), having the Formulas (15A) and (15B) respectively, which encompass the compounds of Formulae (10A&B), (11A&B), (12A&B), (13A&B) and (14A&B).

The composition of compounds (15A) and (15B) have a (15A):(15B) molar percent ratio of from 100:0 to 0:100. Preferably, the composition contains one of the compounds (15A) or (15B) in excess, and more preferably has a (15A):(15B) molar percent ratio of about (100-75):(0-25) or about (0-25):(100-75), and still more preferably has a (15A):(15B) molar percent ratio of about (100-90):(0-10) or about (0-10):(100-90), and still more preferably has a (15A):(15B) molar percent ratio of about (100-95):(0-5) or about (0-5):(100-95). Compositions having one of the compounds (15A) or (15B) in essentially isomerically pure form are most preferred, where isomerically pure form means that at least about 98%, and preferably at least about 99% of the composition is a single one of (15A) or (15B).

Compounds (15A) and (15B) have the Formulae (15A) and (15B) respectively,

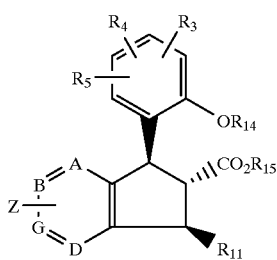

(15A)

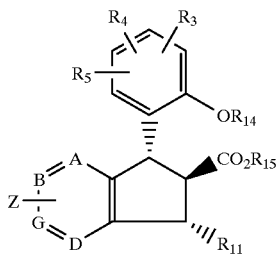

(15B)

or are pharmaceutically acceptable salts thereof.

In Formulae 15A and 15B, $R_2$, $R_3$, $R_4$, $R_5$, A, B, D, G, Z, $R_{11}$, are as defined hereinabove, $R_{12}$ is —$(CH_2)_2OH$ or —$(CH_2)_pCO_2R_{13}$ where p is an integer from 1 to 3;

$R_{13}$ is hydrogen or $C_{1-5}$alkyl;

$R_{14}$ is H, $R_2$, or $R_{12}$;

$R_{15}$ is H, $R_1$ or $R_{13}$;

provided that when $R_{15}$ is H, $R_{14}$ is H or $R_2$.

Particularly preferred compounds of Formula (15A) are the following: methyl-(1S, 2R, 3S)-1-(3,4-methylenedioxyphenyl)-3-[2-(2,3:5,6-di-O-isopropylidene-α-D-mannofuranosyloxy)-4-methoxyphenyl]-5-(prop-1-yloxy)indane-2-carboxylate; (1S, 2R, 3S)-1-(3,4-methylenedioxyphenyl)-3-[2-(2,3:5,6-di-O-isopropylidene-α-D-mannofuranosyloxy)-4-methoxyphenyl]-5-(prop-1-yloxy)indane-2-carboxylic acid; (1S, 2R, 3S)-1-(3,4-methylenedioxyphenyl)-3-(4-methoxy-2-hydroxyphenyl)-5-(prop-1-yloxy)indane-2-carboxylic acid; methyl-(1S, 2R, 3S)-1-(3,4-methylenedioxyphenyl)-3-(4-methoxy-2-hydroxyphenyl)-5-(prop-1-yloxy)indane-2-carboxylate; and methyl-(1S, 2R, 3S)-1-(3,4-methylenedioxyphenyl)-3-[2-(2-hydroxyeth-1-yloxy)-4-methoxyphenyl]-5-(prop-1-yloxy)indane-2-carboxylate.

Thus utilizing the techniques described herein, and as examplified in the following examples, (+)(1S, 2R, 3S) 3-(2-carboxymethyoxy-4-methoxyphenyl)-1-(3,4-metylenedioxyphenyl)-5-(prop-1-yloxy)indane-2-carboxylic acid and (+)(1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and pharmacuetically acceptable salts thereof, having the chemical structures 20 and 21, respectively depicted hereinbelow, to provide a compound of structure 5A and 5B (Structures 23 and 24).

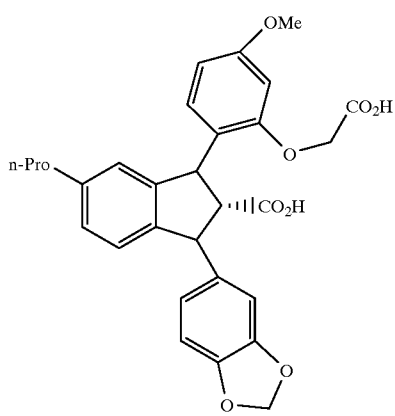

(20)

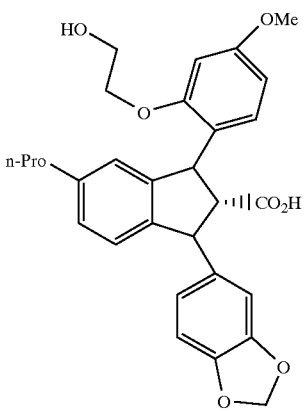

(21)

are synthesized in an efficient and economical manner. For example, an exemplary procedure for synthesizing Compound 20 and 21, is as follows starting from 2-Bromo-3-hydroxyanisole (a compound of Formula 1 wherein $R_1$ is bromo, $R_3$ and $R_5$ are hydrogen and $R_4$ is 4-methoxy). This is reacted with base followed by reaction with 2,3:5,6-di-O-isopropylidene-α-D-mannofuranosyl chloride to form a compound of Formula 3 wherein $R_2$ is 2,3:5,6-di-O-isopropylidene-α-D-mannofuranosyl, and $R_1$, $R_3$, $R_4$ and $R_5$ are as defined hereinabove. The compound of Formula 3 is converted to the Grignard reagent which is reacted with a compound of Formula 4 having structure 22

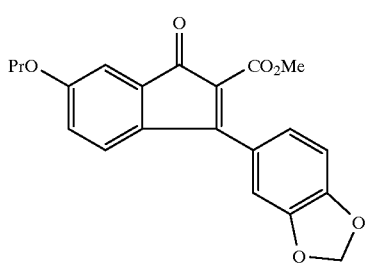

(22)

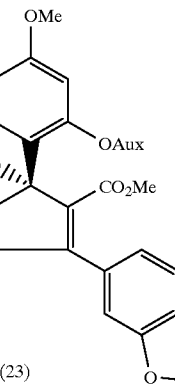

(23)

+

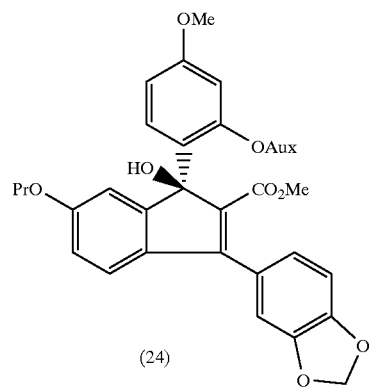

(24)

wherein

Aux = 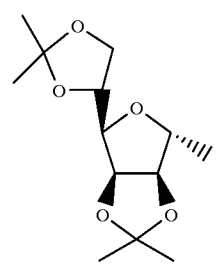

Utilizing the crystallization techniques described hereinabove, compound 23 is isolated and hydrogenated under the reaction conditions described herein to provide a compound of Formula 6A (25).

(25)

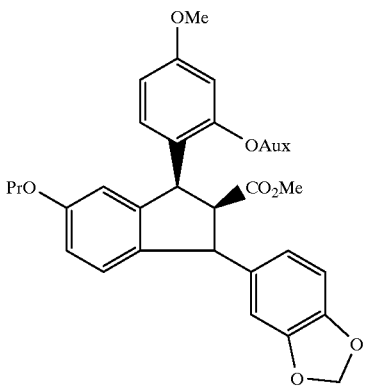

To synthesize compound 20, in one embodiment, 25 is reacted with acid followed by alkylation with L—(CH$_2$)$_p$CO$_2$R$_{13}$ such as methyl bromoacetate, (wherein L is Bromo, p is 1, and R$_3$ is CH$_3$) in base, and then the product thereof is reacted with aqueous base, such as aqueous hydroxide. On the other hand, compound 21 is synthesized, as another embodiment by reacting 25 with acid then by alkylating with ethylene carbonate in the presence of base, e.g., potassium carbonate and then reacting the product thereof with aqueous base, in accordance with the procedure described herein.

Thus the process of the present invention forms compounds of Formulae 7A and 7B as well as the precursors thereof as substantially pure compounds. In addition, they are substantially enantiomerically pure and diasteromerically pure. By substantially, it is meant that the purify is at least 75% and more preferably at least 90%, and even more preferably at least 95% pure, and most preferably 98% pure in the categories emphasized.

The invention will now be illustrated in more detail by the following non-limiting examples, which demonstrate the advantageous properties of the present invention. Parts and percentages are by weight unless indicated otherwise.

EXAMPLE 1
Preparation of 2-bromo-5-methoxyphenyl 2,3:5,6-di-O-isopropylidene-a-D-mannofuranoside with potassium t-butoxide in DME-THF To a stirred solution of 2-bromo-5-methoxyphenol (420 g, 2.07 mol) in 2.5 L of 1,2-dimethoxyethane under a nitrogen atmosphere at 0° C. was added a 1 M solution of potassium t-butoxide in tetrahydrofuran (3.10 L, 3.1 mol). The solution was stirred for 15 minutes then 2,3:5,6-di-O-isopropylidene-a-D-mannofuranosyl chloride (810 g, 2.91 mol) in 1.68 L of 1,2-dimethoxyethane was added over 15 minutes. The reaction mixture was refluxed for 90 minutes. The reaction was quenched with 420 mL of water, then 5.0 L of toluene and 10.1 L of a 2.5 N aqueous sodium hydroxide solution was added and the reaction was stirred for 5 minutes. The aqueous layer was separated and the organic layer was washed twice with 2.5 L portions of 2.5 N aqueous sodium hydroxide solution. The organic solution was concentrated in vacuo to 50% of it's original volume and 500 g of Florisil™ was added. The solution was stirred for 25 minutes then filtered through a pad of 1.0 kg of Aluminum oxide and 420 g of Florisil™. The filter pad was washed with 6 L of 10% ethyl acetate in toluene. The filtrate was concentrated to approximately 1.5 L which weighed 1247.9 g. The concentrate was assayed vs. a reference sample of the title compound. HPLC wt/wt assay indicated 68.0% wt/wt which represents 848.6 g of 2-bromo-5-methoxyphenyl 2,3:5,6-di-O-isopropylidene-a-D-mannofuranoside, (92.1% yield, corrected). An analytical sample was prepared by flash column chromatography on silica gel eluting with ethyl acetate:hexane 20:80.

$^1$H NMR (CDCl$_3$), d (ppm) 7.42 (d, 1H, J=8.8 Hz), 6.52 (dd, 1H, J=2.7 and 8.8 Hz), 5.63 (S, 1H), 4.98 (m, 2H), 4.45 (m, 1H), 4.2 (dd, 1H, J=2.9 and 7.9 Hz), 4.11 (½d$_{AB}$, 1H, J$_{AB}$=8.75 and 6.3 Hz), 4.01 (½d$_{AB}$, 1H, J$_{AB}$=8.75 Hz and 6.3 Hz), 3.79 (s, 3H), 1.43 (m, 12 H). Anal. calc. for C$_{19}$H$_{25}$BrO$_7$; C;51.24, H:5.66, Found; C: 51.27, H: 5.72. m.p. 67–68° C.

EXAMPLE 2
Preparation of 2-bromo-5-methoxyphenyl 2,3:5,6-di-O-isopropylidene-a-D-mannofuranoside with potassium t-butoxide in DME-THF with isolation To a stirred solution of 2-bromo-5-methoxyphenol (500.0 g, 2.46 mol) in 3.00 L of 1,2-dimethoxyethane under a nitrogen atmosphere at 25° C. was added 1 M solution of potassium t-butoxide in tetrahydrofuran (3.69 L, 3.69 mol) at such a rate as to keep the temperature below 35° C. The solution was stirred for 15 minutes then 2,3:5,6-di-O-isopropylidene-a-D-mannofuranose (960.3 g, 3.45 mol) in 2.00 L of 1,2-dimethoxyethane was added over 20 minutes. The reaction mixture was heated to reflux and held at reflux for 2 hours. The reaction was cooled to 25–27° C. and quenched with 250 mL of water, then 1.75 mL of toluene and 1.50 L of a 2.5 N aqueous sodium hydroxide solution were added and the reaction was stirred for 5 minutes. The aqueous layer was separated and the organic layer was washed twice with 1.50 L portions of 2.5 N aqueous sodium hydroxide solution. The organic solution was then washed with 1.50 L of saturated sodium chloride solution and 1.5 L of water. The organic layer was concentrated to approximately 2.0 L under vacuum and filtered. Isopropanol (1 L) was added and the solution was concentrated to a volume of approximately 1.0 L. An additional 1.0 L of isopropanol was added the solution was again concentrated to a volume of approximately 1.0 L. Isopropanol (1 L) was added and the solution was cooled to 0° C. and seed crystals of the title compound added. The solution was stirred at 0° C. for 16 hours then filtered and washed with isopropanol (2×500 mL). The product was dried at 0.1 Torr at 25° C. for 72 hours to afford 878.3 g of the title compound as a white solid (80.2% yield).

$^1$H NMR (CDCl$_3$), d (ppm) 7.42 (d,1H, J=8.8 Hz), 6.52 (dd, 1H, J=2.7 and 8.8 Hz), 5.63 (S, 1H), 4.98 (m, 2H), 4.45 (m, 1H), 4.2 (dd, 1H, J=2.9 and 7.9 Hz), 4.11 (½d$_{AB}$, 1H, J$_{AB}$=8.75 and 6.3 Hz), 4.01 (½d$_{AB}$, 1H, J$_{AB}$=8.75 Hz and 6.3 Hz), 3.79 (s, 3H), 1.43 (m, 12 H). Anal. calc. for C$_{19}$H$_{25}$BrO$_7$; C;51.24, H:5.66, Found; C: 51.27, H: 5.72. m.p. 67–68° C.

EXAMPLE 3
Preparation of 2-bromo-5-methoxyphenyl 2,3:5,6-di-O-isopropylidene-a-D-mannofuranoside with NaH in DME To a stirred suspension of NaH (3 g, 60% dispersion in mineral oil, 75 mmol) in 50 mL of dimethoxy ethane (DME) was added a solution of 2-bromo-5-methoxyphenol (10.15 g, 50 mmol) in 50 mL of DME at 20–25° C. under an atmosphere of nitrogen. After the addition of 2-bromo-5-methoxyphenol, the reaction was stirred for 10 minutes and then a solution of 2,3:5,6-di-O-isopropylidene-a-D-mannofuranosyl chloride (16.7 g, 60 mmol) in 150 mL of DME was added at 40–45° C. After the addition, the reaction mixture was heated to 80–85° C. and kept at this temperature for approximately 5 hours. The reaction was quenched with 5 mL of water and concentrated in vacuo. To the concentrate, 300 mL of t-butyl methyl ether was added followed by 150 mL of water and the resulting solution stirred for 5 minutes before the organic phase was separated. The aqueous layer was back-extracted with 100 mL of t-butyl methyl ether. The combined organics were washed with 10% aqueous NaOH solution (2×120 mL), followed by 200 mL of brine. The organic solution was then dried over MgSO$_4$, filtered and treated with activated carbon (Darco) by heating to 55° C. for 5 minutes. After removing the activated carbon by filtration through Celite, the filtrate was concentrated in vacuo. The concentrate was taken up into 40 mL of CH$_2$Cl$_2$ and passed through a pad of basic aluminum oxide by eluting with 600 mL of 20% EtOAc in hexane. The elute was concentrated in vacuo to afford 15.7 g (70.5%) of 2-bromo-5-methoxyphenyl 2,3:5,6-di-O-isopropylidene-a-D-mannofuranoside as a light yellow oil. The HPLC analysis (CH$_3$CN/H$_2$O=65/35, 1.0 mL/min, Inertsil C18, 5 m, 4.6 mm×30 mm, l=220 nm) indicated 96% (PAR) of title compound together with 3% (PAR) of the b-anomer, 2-bromo-5-methoxyphenyl 2,3:5,6-di-O-isopropylidene-b-D-mannofuranoside.

EXAMPLE 4
Preparation of 2-bromo-5-methoxyphenyl 2,3:5,6-di-O-isopropylidene-a-D-mannofuranoside and 2-bromo-5-methoxyphenyl 2,3:5,6-di-O-isopropylidene-b-D-mannofuranoside with DBU as the base In a similar manner to that described above 2-bromo-5-methoxyphenol (0.99 g, 4.67 mmol) in 15 mL of toluene, 0.73 g (4.79 mmol) of 1,8-diazobicylclo[5,4,0]undec-7-ene (DBU) and 2,3:5,6-di-O-isopropylidene-a-D-mannofuranosyl chloride (1.3 g, 4.87 mmol) were heated at 100° C. for approximately 20 hours to afford a mixture of the title compounds in a ratio of 3:2 (as judged by HPLC peak area ratio). The reaction was worked up in a similar manner to that described above and the title compounds isolated by column chromatoghaphy eluting with ethyl acatate and hexane.

$^1$H NMR (CDCl$_3$) for 2-bromo-5-methoxyphenyl 2,3:5,6-di-O-isopropylidene-b-D-mannofuranoside, d (ppm) 7.40 (d, 1H, J=8.7 Hz), 6.7 (d, 1H, J=2.8 Hz), 6.5 (dd, 1H, J=8.8 and 2.7 Hz), 5.3 (d, 1H, J=3.7 Hz), 4.8 (m, 2H), 4.6–4.5 (m, 1H), 4.1–1.0 (m, 2H), 3.9 (q, 1H, J=3.8 and 7.8 Hz) 3.8 (s, 3H), 1.6 (s, 3H), 1.45 (s, 3H), 1.43 (s, 3H), 1.38 (s,3H).

EXAMPLE 5
Preparation of 2-(2,3:5,6-di-O-isopropylidene-a-D-mannofuranosyloxy) chlorobenzene To a stirred solution of 2-chlorophenol (1.24 g, 1.0 mL, 9.6 mmol) in 12 mL of 1,2-dimethoxyethane under a nitrogen atmosphere at 0° C. was added a 1 M solution of potassium t-butoxide in hexane (14.0 mL, 14 mmol). The solution was stirred for 5 minutes then 2,3:5,6-di-O-isopropylidene-a-D-mannofuranosyl chloride (3.30 g, 12 mmol) in 10 mL of 1,2-dimethoxyethane was added over 5 minutes. The reaction mixture was refluxed for 90 minutes. The reaction was quenched with 2 mL of water, then 50 mL of ethyl acetate and 40 mL of a 2.5 N aqueous sodium hydroxide solution were added and the reaction was stirred for 5 minutes. The aqueous layer was separated and back extracted with 50 mL of ethyl acetate. The organic solution was concentrated in vacuo to a yellow-brown oil. This oil was purified by silica gel flash column chromatography (ethyl acetate/hexane=1/10) to afford 2.88 g (79%) of the title compound as a white crystalline solid. An analytical sample was prepared by preparative chromatography using reverse phase plates purchased from Chem Dynamics (86-7827-70, RP-18/UV 254, 1 mm thickness) developing with acetonitrile/water (60:40).

$^1$H NMR (CDCl$_3$), d (ppm) 7.39 (dd, 1H, J=1.2, 8 Hz), 7.28 (2×dd, 2H, J=1.3, 8.4 Hz), 7.00 (ddd, 1H, J=1.0, 6.9, 8, Hz), 5.63 (s, 1H), 4.95 (m, 2H), 4.43 (m, 1H), 4.18 (dd, 1H, J=2.9, 7.9 Hz), 4.09 (dd, 1H, J=6.2, 8.7 Hz), 3.98 (dd, 1H, J=4.2, 8.7 Hz), 1.43 (m, 12 H). Anal. calc. for C$_{18}$H$_{23}$O$_6$Cl; C: 58.29, H: 6.25, Found; C: 58.19, H: 6.13.

EXAMPLE 6
Preparation of 2,6-Dimethyl-4-(2,3:5,6-di-O-isopropylidene-a-D-mannofuranosyloxy) bromobenzene To a stirred solution of 4-bromo-3,5-dimethylphenol (2.01 g, 10 mmol) in 12 mL of 1,2-dimethoxyethane under a nitrogen atmosphere at 0° C. was added a 1 M solution of potassium t-butoxide in hexane (15.0 mL, 15 mmol). The solution was stirred for 5 minutes then 2,3:5,6-di-O-isopropylidene-a-D-mannofuranosyl chloride (3.90 g, 14 mmol) in 8 mL of 1,2-dimethoxyethane was added over 5 minutes. The reaction mixture was refluxed for 90 minutes. The reaction was quenched with 2 mL of water, then 25 mL of toluene and 50 mL of a 2.5 N aqueous sodium hydroxide solution were added and the reaction was stirred for 5 minutes. The aqueous layer was separated and the organic layer was washed with 2×25 mL portions of 2.5 N aqueous sodium hydroxide solution. The organic solution was concentrated in vacuo to 50% of it's original volume and 5 g of Florisil™ was added. The solution was stirred 10 minutes then filtered through a pad of 10 g of Aluminum oxide and 5 g of Florisil™. The filter pad was washed with 100 mL of 10% ethyl acetate in toluene. The filtrate was concentrated to afford 4.71 g of the title compound. An analytical sample was prepared by preparative chromatography using reverse phase plates purchased from Chem Dynamics (86-7827-70, RP-18/UV 254, 1 mm thickness) developing with acetonitrile/water (60:40).

$^1$H NMR (CDCl$_3$), d (ppm) 6.75 (s, 1H), 5.60 (s, 1H), 4.90 (m, 1H), 4.85 (m, 1H), 4.45 (m, 1H), 4.15 (m, 1H), 4.10 (m, 1H), 4.00 (m, 1H), 2.35 (s, 6H), 1 45 (m, 12H). Anal. calc. for C$_{20}$H$_{27}$BrO$_6$; C;54.18, H:6.14, Found; C: 54.46, H: 5.78.

EXAMPLE 7
Preparation of (R) and (S)-methyl-3-(3,4-methylenedioxyphenyl-1-hydroxy-1-[2-(2,3:5,6-isopropylidene-a-D-mannofuranosyloxy-4-methoxyphenyl]-6-propoxy-1H-indene-2-carboxylate Method 1: Halogen Metal Exchange Followed by Transmetallation To a stirred solution of 2-bromo-5-methoxyphenyl 2,3:5,6-di-O-isopropylidene-a-D-mannofuranoside (303.8 g, 68% wt/wt assay in toluene, 463.9 mmol) in 1.7 L of THF under a nitrogen atmosphere at −75° C. was added 185 mL of n-BuLi (24% solution in hexane, nominally 2.6 M) over 30 minutes. The solution was stirred for 5 minutes then approximately 0.1 mL of this solution was taken for HPLC analysis to ensure complete metal-halogen exchange. With moderate agitation, MgBr$_2$.Et$_2$O (180 g, 697.1 mmol) was added at −78 to −75° C. After the addition of MgBr$_2$.Et$_2$O, the resulting suspension was warmed to 22–25° C. over 80 minutes so that the reaction mixture was a clear solution. This solution was stirred for another 2 hours before it was cooled back to −78° C. To the slightly cloudy solution at −78° C., a solution of methyl 3-(1,3-benzodioxol-5-yl)-1-oxo-propoxy-1H-indene-2-carboxylate (110 g, 297 mmol) in 1.1 L of THF) was added slowly so that the internal temperature did not go above −72° C. The reaction mixture was stirred for 5 minutes after the addition was complete and a small amount of the mixture removed for HPLC analysis. The ratio of two diastereomeric products was 88:12 with the (R)-isomer as the major one by HPLC (PAR). The reaction was quenched with 100 mL of 20% aqueous solution of $NH_4Cl$ at about −72° C. and warmed to 22–25° C. The resulting mixture was concentrated from 3.5 L to 3.0 L by distillation. After concentration, 1 L of water was added and the mixture was stirred for 5 minutes. The aqueous layer was separated and back extracted with 300 mL of toluene. The organic solution was washed with 500 mL of water to yield a mixture of crude (R)- and (S)-methyl-3-(3,4-methylenedioxyphenyl)-1-hydroxy-1-[2-(2,3:5,6-isopropylidene-a-D-mannofuranosyloxy-4-methoxyphenyl]-6-propoxy-1H-indene-2-carboxylate (88 to 12) as a solution in THF and toluene.

Method 2: Direct Grignard Method

To a stirred solution of 2-bromo-5-methoxyphenyl 2,3:5,6-di-O-isopropylidene-a-D-manno-furanoside (0.2 g, 0.45 mmol) in anhydrous tetrahydrofuran (THF) (3 mL) under a nitrogen atmosphere at 18° C. was added Mg (0.15 g, 6.25 mmol). To this mixture, 1,2-dibromoethane (50 mL, 0.59 mmol) was added. The temperature of this mixture went up from 18° C. to 23° C. over approximately 10 minutes. At this time, a solution of 2-bromo-5-methoxyphenyl 2,3:5,6-di-O-isopropylidene-a-D-mannofuranoside (1.8 g, 4.04 mmol) in anhydrous THF (12 mL) was added slowly at 25–31° C. over 10 minutes. After the addition, the Grignard reagent was stirred for 30 minutes and checked by HPLC. This solution was then added via a cannular into a suspension of methyl 3-(1,3-benzodioxol-5-yl)-1-oxo-6-propoxy-1H-indene-2-carboxylate (1.07 g, 2.92 mmol) in anhydrous THF (10 mL) at between −70 and −65° C. over 10 minutes. After this addition, the reaction mixture was warmed from −70° C. to −5° C. over approximately 15 minutes and a small aliquot was taken for HPLC analysis. The ratio of the two diastereomeric products was determined to be 85 to 15 with the (R)-isomer as the major one by HPLC (PAR). The reaction mixture was quenched with aqueous $NH_4Cl$ solution (17%, 1.5 mL). The quenched mixture was evaporated under reduced pressure then taken up into EtOAc (15 mL). This organic mixture was washed with aqueous citric acid solution (3%, 25 mL), followed by $H_2O$ (2×30 mL) to neutral pH. From this crude eaction mixture, (R)-methyl-3-(3,4-methylenedioxyphenyl)-1-hydroxy-1-[2-(2,3:5,6-isopropylidene-a-D-mannofuranosyl-oxy-4-methoxyphenyl]-6-propoxy-1H-indene-2-carboxylate could be isolated as described below.

EXAMPLE 8

Isolation of (R)-methyl-3-(3,4-methylenedioxyphenyl)-1-hydroxy-1-[2-(2,3:5,6-isopropylidene-a-D-mannofuranosyloxy-4-methoxyphenyl]-6-propoxy-1H-indene-2-carboxylate A mixture of (R)- and (S)-methyl-3-(3,4-methylenedioxyphenyl)-1-hydroxy-1-[2-(2,3:5,6-isopropylidene-a-D-mannofuranosyloxy-4-methoxyphenyl]-6-propoxy-1H-indene-2-carboxylate preprared as described above (either by Method 1 or 2), ratio 88:12 R to S, in THF and toluene (3500 mL) was concentrated in vacuo at 25–50° C. to a volume of approximately 300–350 mL. To this concentrate, 550 mL of n-butanol was added. The resulting red-brown solution was concentrated in vacuo at 50–57° C. to a volume of 400–450 mL. The concentrate was cooled and 100 mL of water was added. The resulting slurry was cooled to 30–35° C. before it was seeded. After seeding, the slurry was stirred at 20–25° C. for 20 hours, and the desired (R)-isomer precipitated out slowly during this stir period. The product was isolated by vacuum filtration and rinsed with 2×110 mL portions of n-butanol followed by 2×110 mL portions of hexane to yield after drying, 152 g (69% yield) of the title compound. Analysis indicated 98.4% wt/wt and 99.5% d.e. An analytical sample was prepared by recrystallization from n-butanol/water.

$^1$H NMR (CDCl$_3$), d (ppm) 7.96 (1H, d, J=8.7 Hz), 7.19 (1H, d, J=8.4 Hz), 7.08–7.03 (2H, m), 6.92 (1H, d, J=7.9Hz), 6.78 (1H, dd, J=3.3, 8.4 Hz), 6.72 (1H, d, J=2.3 Hz), 6.69 (1H, dd, J=2.6, 8.7 Hz), 6.55 (1H, d, J=2.3 Hz), 6.04 (2H, AB, J=6.1 Hz), 5.46 (1H, s), 4.41–4.37 (2H, t), 4.22–4.18 (2H, m), 3.97–3.82 (2H, m), 3.79 (3H, s), 3.68 (1H, qt, J=4.8, 8.7 Hz), 3.56 (3H, s), 2.90 (1H, qt, J=4.7, 8.0 Hz), 1.72 (2H, qt, J=6.9, 14.1 Hz), 1.41 (3H, s), 1.33 (3H, s), 1.30 (3H, s), 1.15 (3H, s), 0.97 (3H, t, J=7.5 Hz). Anal. calc. for $C_{40}H_{44}O_{13}$; C:65.56, H:6.05, Found; C:65.46, H: 6.02.

EXAMPLE 9

Isolation of (S)-methyl-3-(3,4-methylenedioxyphenyl)-1-hydroxy-1-[2-(2,3:5,6-isopropylidene-a-D-mannofuranosyloxy-4-methoxyphenyl]-6-propoxy-1H-indene-2-carboxylate (S)-methyl-3-(3,4-methylenedioxyphenyl)-1-hydroxy-1-[2-(2,3:5,6-isopropylidene-a-D-mannofuranosyloxy-4-methoxyphenyl]-6-propoxy-1H-indene-2-carboxylate was isolated by reverse phase preparative chromatography on a Waters Prep 500 eluting with ethyl acetate and hexane (85:15) as the eluents.

$^1$H NMR (CDCl$_3$), d (ppm) 7.96 (1H, d, J=8.7 Hz), 7.25 (1H, m), 7.03–7.0 (2H, m), 6.89 (1H, dd, J=7.7 and 0.9 Hz), 6.81–6.74 (m, 2H), 6.7 (1H, dd, J=8.6 and 2.5 Hz), 6.59 (1H, d, J=2.5 Hz), 6.04 (2H, s), 5.16 (1H, s), 4.5 (1H, dd, J=5.8 and 3.7 Hz), 4.3–4.21 (2H, m), 3.9–3.8 (6H, m), 3.57 (3H, s), 1.75 (2H, dd, J=6.7 and 4.0 Hz), 1.39 (3H, s), 1.38 (3H, s), 1.34 (3H, s), 1.24 (3H, s), 0.98 (3H, s).

EXAMPLE 10

Preparation of methyl-(1S,2S,3S)-1-(3,4-methylenedioxyphenyl)-3-[2-(2,3:5,6-di-O-isopropylidene-a-D-mannofuranosyloxy-4-methoxyphenyl]-5-(prop-1-yloxy)indane-2-carboxylate A 5 gallon Hastelloy-C reactor and all necessary equipment was inspected for cleanliness and dryness. The vessel was pressure tested to 100 psi to determine the leak rate. When an acceptable leak rate was established, the reactor was flushed with nitrogen and residual oxygen levels determined. When acceptable levels of oxygen were detected, the vessel was charged with 12 L of ethyl acetate, 1.26 kg (97.9%, 1.68 mol) of (R)-methyl-3-(3,4-methylenedioxyphenyl)-1-hydroxy-1-[2-(2,3:5,6-isopropylidene-a-D-mannofuranosyloxy-4-methoxyphenyl]-6propoxy-1H-indene-2-carboxylate and 500 g of 15% Pd/C 1910 (approximately 50% water wet) purchased from Precious Metals Corporation. The vessel was sealed, then pressurised to approximately 100 psi with nitrogen, then vented to the atmosphere. This procedure was repeated an additional 2 times. After the third cycle, the reactor leak rate was monitored for approximately 5 minutes. When a satisfactory leak rate was established, the nitrogen was vented to the atmosphere and the vessel pressurised to 100 psi with hydrogen. The hydrogen was released to the atmosphere and the cycle repeated an additional 2 times. After the third cycle, the vessel was re-pressurised with hydrogen to approximately 100 psi and the agitator started. The agitator was set at 700–750 rpm. The progress of the reaction was monitored by in-process HPLC analysis and by the recorded hydrogen uptake. The reaction was deemed complete after 4 hours at ambient temperature and 100 psi hydrogen pressure after a theoretical uptake of hydrogen had been recorded (typically pressures of between 80–100 psi hydrogen pressure are optimal). The hydrogen was vented to the atmosphere and the vessel purged 3 times with nitrogen. After each purge, the nitrogen was vented to the atmosphere. The contents of the vessel were drained into a clean poly drum and the reactor rinsed with 4 L of ethyl acetate. The combined organics were filtered through approximately 500 g of celite, washing with ethyl acetate to yield 27 L of an ethyl acetate solution of crude SB 223222, 80.7% PAR by HPLC.

EXAMPLE 11

Isolation of methyl-(1S,2S,3S)-1-(3,4-methylenedioxyphenyl)-3-[2-(2,3:5,6-di-O-isopropylidene-a-D-mannofuranosyloxy-4-methoxyphenyl]-5-(prop-1-yloxyl)indane-2-carboxylate A glass-lined 10 gallon reactor, and all necessary equipment was inspected for cleanliness and dryness. Via filtration through a 1 micron filter, 54 L of a solution of crude methyl-(1S,2S,3S)-1-(3,4-methylenedioxyphenyl)-3-[2-(2,3:5,6-di-O-isopropylidene-a-D-mannofuranosyloxy-4-methoxyphenyl]-5-propoxyindane-2-carboxylate was added. At atmospheric pressure, the solution was concentrated by distillation at atmospheric pressure to a final volume of approximately 18 L. Ethanol (24 L) was added to the concentrate and the resulting mixture concentrated down at atmospheric pressure to a volume of 18–20 L. Additional ethanol (24 L) was added resulting in the precipitation of the title compound. The slurry was concentrated again at atmospheric pressure to a volume of 24 L before the addition a third ethanol chase (24 L). The resulting slurry was concentrated at atmospheric pressure to a final volume of approximately 24 L, then allowed to cool to ambient temperature overnight. After stirring for approximately 12–16 hours at ambient temperature, the slurry was cooled to 0–5° C. and stirred at this temperature for approximately 3 hours before isolation of the product by centrifugation. The solids were washed with ethanol (12 L of 200 proof chilled to 0–5° C.) then dried to constant weight to yield 1.90 kg (75.1% corrected yield) of the title compound as a white crystalline solid. Analysis indicated >99.9% de by HPLC. [Yields for this conversion are typically in the range 60–80%.]

$^1$H NMR (CDCl$_3$), d 7.32 (1H, d, J=8.6 Hz), 7.08 (1H, q, J=8.3 and 1.2Hz), 6.74–6.89 (6H, m), 6.55 (1H, q, J=8.7 and 2.6 Hz), 5.93 (1H, q, J=2.9 and 1.5 Hz), 5.68 (1H, s), 4.94–5.01 (3H, m), 4.69 (1H, d, J=7.6 Hz), 4.44–4.49 (1H, m), 4.22 (1H, q, J=3.5 and 7.6 Hz), 4.13 (1H, q, J=6.3 and 8.7 Hz), 4.04 (1H, q, J=4.6 and 8.7Hz), 3.90 (2H, t, J=6 Hz), 3.84 (1H, t, J=8 Hz), 3.80 (s, 3H), 2.96 (s, 3H), 1.77–1.82 (m, 2H), 1.54 (s, 3H), 1.43 (s, 3H), 1.41 (s, 3H),1.39 (s, 3H), 1.03 (t, 3H, J=7.4 Hz).

EXAMPLE 12

Preparation of methyl-(1R,2R,3R)-1-3,4-methylenedioxyphenyl-3-[2-(2,3:5,6-di-O-isopropylidene-a-D-mannofuranosyloxy-4-methoxyphenyl]-5-propoxyindane-2-carboxylate A 100 mL miniclave was charged with 15 mL of ethyl acetate, 15 mL of ethanol (200 proof), 130 mg of (S)-methyl-3-(3,4-methylenedioxyphenyl)-1-hydroxy-1-[2-(2,3:5,6-isopropylidene-a-D-mannofuranosyloxy-4-methoxyphenyl]-6-propoxy-1H-indene-2-carboxylate and 64 mg of 10% Pd on Carbon (on a dry basis). The vessel was sealed, then pressurised to approximately 400 psi with nitrogen, then vented to the atmosphere. This procedure was repeated an additional 2 times. After the third cycle, the reactor leak rate was monitored for approximately 5 minutes. When a satisfactory leak rate was established, the nitrogen was vented to the atmosphere and the vessel pressurised to 100 psi with hydrogen. The hydrogen was released to the atmosphere and the cycle repeated an additional 2 times. After the third cycle, the vessel was re-pressurized with hydrogen to approximately 400 psi, the internal contents warmed to 55° C. and the agitator started. The reaction was deemed complete after 24 hours. The hydrogen was vented to the atmosphere and the vessel purged 3 times with nitrogen. After each purge, the nitrogen was vented to the atmosphere. The contents of the vessel were drained into a clean container and the reactor rinsed with 20 mL of ethyl acetate. The combined organics were filtered through approximately 5 g of celite, washing with ethyl acetate to yield after concentration the title product. The crude material was purified by crystallization from methanol to yield 64 mg (50.3%) of the title compound as white needles. Analysis indicated >99.9% de by HPLC.

$^1$H NMR (CDCl$_3$), d 7.29 (1H, d, J=8.6 Hz), 7.08 (1H, d, J=8.1 Hz), 6.73–6.87 (6H, m), 6.52 (1H, q, J=8.6 and 2.5 Hz), 5.93 (1H, q, J=2.9 and 1.5 Hz), 5.69 (1H, s), 4.94–4.97 (3H, m), 4.71 (1H, d, J=7.7 Hz), 4.44–4.49 (1H, m), 4.12–4.14 (2H, m), 4.04 (1H, q, J=4.6 and 8.7 Hz), 3.91 (2H, t, J=6 Hz), 3.84 (1H, t, J=8 Hz), 3.78 (s, 3H), 2.97 (s, 3H), 1.77–1.82 (m, 2H), 1.54 (s, 3H), 1.43 (s, 3H), 1.41 (s, 3H), 1.39 (s, 3H), 3.80 (t, 3H, J=7.4 Hz).

EXAMPLE 13

Preparation of methyl-(1S,2R,3S)-1-(3,4-methylenedioxyphenyl)-3-(4-methoxy-2-hydroxyphenyl)-5-(prop-1-yloxy)indane-2-carboxylate To a solution of methyl-(1S,2S,3S)-1-(3,4-methylenedioxyphenyl)-3-[2-(2,3:5,6-di-O-isopropylidene-a-D-mannofuranosyloxy-4-methoxyphenyl]-5-propoxyindane-2-carboxylate (100 g, 0.139 mol) in THF (900 mL) and methanol (400 mL) was added a solution of lithium hydroxide (29.2 g, 0.695 mol) in water (360 mL). The reaction mixture was heated to reflux and monitored by HPLC. The reaction was complete in 2.5 hours. The reaction was cooled to 20–25° C. and 1.57 L of toluene and a solution of 100 g of citric acid in 1.5 L of water was added. The layers were separated and the aqueous layer was extracted with 1.57 L of toluene. The combined toluene layers were washed with 2 portions of 5% aqueous sodium bicarbonate (1.2 L) and concentrated under reduced pressure to approximately 250 mL. The toluene solution of (1S, 2R, 3S)-1-(3,4-methylenedioxyphenyl)-3-[2-(2,3:5,6-di-O-isopropylidene-a-D-mannofuranosyloxy-4-methoxyphenyl]-5-propoxyindane-2-carboxylic acid was filtered through Celite and methanol (1000 mL) was added. Concentrated hydrochloric acid (49.5 mL) was added in one portion and the solution was heated to reflux. The reaction was monitored by HPLC and was complete in approximately 2 hours. The reaction mixture was cooled to 20–25° C. and 100 mL of water and 250 mL of toluene was added. The solution was concentrated under reduced pressure to approximately 400 mL. Toluene (750 mL) and water (100 mL) were added, followed by 5% sodium bicarbonate solution (260 mL). The layers were separated and the organic layer was washed twice with 5% sodium bicarbonate solution (2×260 mL). The organic layer was concentrated to about 200 mL under reduced pressure, toluene (300 mL) was added, then the solution was filtered through Celite. The filtrate was concentrated to approximately 500 mL to afford approximately a 15–20% solution of methyl-(1S, 2R, 3S)-1-(3,4-methylenedioxyphenyl)-3-(4-methoxy-2-hydroxyphenyl)-5-propoxyindane-2-carboxylate in toluene. The final solution was sampled for assay and found to contain 14.6% of the desired material. This represents 66.27 g of product (99.6% yield, corrected). A sample was concentrated under reduced pressure for spectral analysis:

$^1$H NMR (CDCl$_3$), d 7.0 (d, 1H), 6.82–6.68 (m, 5 H), 6.58–6.48 (m, 2H), 5.95 (d, 2 H), 4.9 (d, J=10.5 Hz, 1 H), 4.40 (d, J=10.5 Hz, 1H), 3.83 (m,2 H), 3.78 (s, 3H), 3.70 (s, 3H), 3.25 (t, J=10.5 Hz, 1H), 1.75 (m, 2H), 1.0 (t, 3H) ppm.

EXAMPLE 14

Preparation of methyl-(1S,2S,3S)-1-(3,4-methylenedioxyphenyl)-3-(4-methoxy-2-hydroxyphenyl)-5-(prop-1-yloxy)indane-2-carboxylate A 5 L 3 necked round-bottom flask equipped with an air driven stirrer, reflux condenser and a nitrogen inlet/outlet was charges with 375.0 g (96.1% wt/wt, 501.4 mmol) methyl-(1 S,2S,3S)-1-(3,4-methylenedioxyphenyl)-3-[2-(2,3:5,6-di-O-isopropylidene-a-D-mannofuranosyloxy-4-methoxyphenyl]-5-propoxyindane-2-carboxylate, 3750 mL of methanol and 37.5 mL of concentrated aqueous HCl. The resulting slurry was heated to 60–65° C. under an atmosphere of nitrogen over a period of approximately 60 minutes. When at 63° C., an additional 37.5 mL of concentrated aqueous HCl was added to the mixture and the solution maintained within the temperature range of 60–65° C. The progress of the reaction was monitored by HPLC. The reaction was deemed to be complete when no starting material was detected. The resulting clear solution was allowed to cool towards ambient temperature over a period of approximately 3 hours. When at or below 30° C., 2.0 g of seed crystals of the title compound were added. The resulting slurry was stirred at ambient temperature for approximately 18 hours, then cooled to 0–5° C. for an additional 4 hours. The product was isolated by filtration and washed with 2 portions of methanol (2×500 mL chilled to 0–5° C0. The isolated methyl-(1S, 2S, 3S)-1-(3,4-methylenedioxyphenyl)-3-(4-methoxy-2-hydroxyphenyl)-5-propoxyindane-2-carboxylate was dried under vacuum (30 in. Hg at 30–35° C.) to constant weight over approximately 21 hours to yield 213.0 g (88.0% corrected yield) of the title compound. Analysis indicated 98.4% wt/wt and >99.9% ee by HPLC.

EXAMPLE 15

(+) (1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylic acid ethylene diamine salt (2:1) (Compound)

A 500 mL flask was charged with 150 mL of toluene followed by ethylene carbonate (29.4 g, 98%, 327 mmol) and 15.9 g (97.4%, 32.6 mmol) of methyl-(1S,2S,3S)-1-(3,4-methylenedioxyphenyl)-3-(4-methoxy-hydroxyphenyl)-5-propoxyindane-2-carboxylate. With moderate agitation at ambient temperature, potassium carbonate (23.1 g, 98%, 163.8 mmol) was added. Under an atmosphere of nitrogen and with moderate agitation, the contents of the flask were heated to approximately 112° C. After approximately 3 hours at or around 112° C., the reaction was cooled to 25–30° C. over a period of 20 minutes, and DI water (120 mL) was added. The mixture was stirred then the aqueous layer was separated. The organic phase was concentrated to a gum under reduced pressure then diluted with methanol (50 mL) and tetrahydrofuran (80 mL). A solution of lithium hydroxide monohydrate, 4.5 g (477.8 mmol) dissolved in 50 mL of water was then added. The reaction mixture was heated to reflux (internal temperature 62–65° C.) over approximately 15 minutes and maintained at reflux while monitoring the reaction progress by HPLC. The reaction was considered complete when no intermediates were detected by HPLC analysis. After approximately 60 minutes at reflux the reaction was considered complete and the contents of the flask cooled to ambient and the reaction mixture concentrated under reduced pressure. Toluene (150 mL), water (150 mL) followed by citric acid (15 g) was then added to the resulting solution and the mixture stirred for approximately 15 minutes. The bottom aqueous layer was drained and the organic layer was washed with aqueous brine solution (100 mL). The organic layer was drained from the flask, then concentrated in vacuo to afford 16.2 g of the title compound as a foam.

HPLC wt/wt assay indicated 90.5% purity for a corrected yield of 88.8%

An analytical sample could be obtained by recrystallization from 2-propanol. Mpt. 125–127° C.

A toluene solution of (+)(1S,2R,3S)]-3-[2-(2-hydroxyeth-1-yloxy)-4-methoxyphenyl]-1-(3,4-methylendioxyphenyl)-5-(prop-1-yloxy)indane-2-carboxylic acid (868.8 g @ 11.2% wt/wt, 192.5 mmol) was concentrated under reduced pressure to a volume of approximately 200 mL. Distillation was discontinued and 2-propanol (500 mL) added to the concentrate. The organic solution was concentrated again under reduced pressure to a volume of approximately 200 mL. Distillation was discontinued and 2-propanol (500 mL) added to the concentrate. The resulting solution in 2-propanol was allowed to stir at ambient temperature for approximately 15 minutes to obtain a homogeneous mixture then diluted with an additional 1000 mL of 2-propanol. The resulting solution was heated to approximately 60° C. over a period of 15–20 minutes under a gentle purge of nitrogen. Heating was discontinued and ethylene diamine (11.6 g, 99.5+%, 192.5 mmol) was added. The reaction mixture was cooled to 30–35° C. over a period of 4 hours. As the solution cooled to 57° C., precipitation of the title compound occurred. The resulting slurry was stirred at ambient temperature for approximately 12 hours then cooled to 0° C. an additional 3 hours before isolation of the title compound via filtration. The product was washed with 3 portions of 2-propanol (300 mL) followed by hexane's (600 mL) chilled to 0–5° C. The product was dried in the vacuum oven for approximately 16 hours at 20–25° C. to afford 91.6 (87%) of the title compound.

Anal Calcd. for C30H34NO8 C, 67.15; H, 6.39; N, 2.61. Found, C, 67.2; H,6.48; N, 2.67.

EXAMPLE 16

Methyl-(1S,2R,3S)-1-(3,4-methylenedioxyphenyl)-3-[2-(2,3:5,6-di-O-isopropylidene-a-D-mannofuranosyloxy-4-methoxyphenyl]-5-propoxyindane-2-carboxylate Methyl-(1S,2S,3S)-1-(3,4-methylenedioxyphenyl)-3-[2-(2,3:5,6-di-O-isopropylidene-a-D-mannofuranosyloxy-4-methoxyphenyl]-5-propoxyindane-2-carboxylate (3.5 g, 4.8 mmol) was dissolved in 31.5 mL of tetrahydrofuran and 14.4 mL of water. A solution of lithium hydroxide (1.022 g, 24 mmol) in 14 mL of water was added over a period of 5 minutes. The reaction mixture was heated to reflux temperature while monitoring the reaction progress by HPLC. After 30 minutes at reflux, HPLC analysis indicated that the reaction contained approximately 28% of the title compound by peak area. Approximately one-half of the reaction mixture (30 mL) was removed and analyzed by HPLC/MS to identify this intermediate in the reaction process.

HPLC/MS: HPLC conditions—YMCBasic 4.6×150 mm column, solvent system: 65:35:0.1, acetonitrile:water:trifluoroacetic acid; flow:1 mL/min, UV detection at 220 nm. SB 231701, RRT=1.18. MS: m/z 705 (M+H)$^+$, 687 (M+H–18)$^+$, 647 (M+H–58)$^+$, 629 (M+H–76)$^+$.

EXAMPLE 17
(1S,2R,3S)-1-(3,4-methylenedioxyphenyl)-3-[2-(2,3:5,6-di-O-isopropylidene-a-D-mannofuranosyloxy-4-methoxyphenyl]-5-propoxyindane-2-carboxylic acid Methyl-(1S,2S,3S)-1-(3,4-methylenedioxyphenyl)-3-[2-(2,3:5,6-di-O-isopropylidene-a-D-mannofuranosyloxy-4-methoxyphenyl]-5-propoxyindane-2-carboxylate (5.0 g, 0.70 mmol) was dissolved in 45 mL of tetrahydrofuran and 20 mL of methanol. A solution of lithium hydroxide (1.46 g, 3.47 mmol) in 18 mL of water was added over a period of 5 minutes. The reaction mixture was heated to reflux temperature while monitoring the reaction progress by HPLC. After 2 hours at reflux, HPLC analysis indicated that the reaction was complete. The reaction mixture was cooled to 25° C., then diluted with toluene 40 mL). A 10% solution of citric acid (45 mL) was added and the mixture was stirred for five minutes. The layers were separated and the aqueous layer was extracted with 40 mL of toluene. The combined organic layers were washed twice with 5% sodium bicarbonate 40 mL) and filtered. The solution was concentrated under reduced pressure to afford the title compound as a foam as a foam.

$^1$ H NMR d (CDCl3) 7.30–7.10 (m, 4H), 6.85–6.55 (m, 5H), 6.40 (s, 1H), 5.95 (d, 2H), 5.85 (s, 1H), 4.97 (d, 1H), 4.87 (s, 1H), 4.60 (d, 1H), 4.40 (m, 1H), 4.00 (m, 4H), 3.80 (m, 2H), 3.80 (m, 3H), 3.15 (m, 1H), 1.75 (m. 2H), 1.55 (d, 6H), 1.32 (d, 6H), 1.0 (t, 3H).

EXAMPLE 18
(1S,2R,3S)-1-(3,4-methylenedioxyphenyl)-3-[2-hydroxy-4-methoxyphenyl]-5-propoxyindane-2-carboxylic acid Methyl-(1S,2R,3S)-1-(3,4-methylenedioxyphenyl)-3-(4-methoxy-2-hydroxyphenyl)-5-propoxyindane-2-carboxylate (0.3183 g, 0.667 mmoles) was dissolved in 2 mL of tetrahydrofuran and 4 mL of methanol. A solution of lithium hydroxide (0.1402 g, 3.34 mmoles) in 1.8 mL of water was added over a period in one portion. The reaction mixture was heated to reflux temperature while monitoring the reaction progress by HPLC. After 22 hours at reflux, HPLC analysis indicated that the reaction was complete. The reaction mixture was cooled to 25° C., then diluted with t-butyl methyl ether (5 mL). A 5% solution of citric acid (5 mL) was added and the mixture was stirred for five minutes. The layers were separated and the aqueous layer was extracted with 10 mL of t-butyl methyl ether. The combined organic layers were washed twice with water and filtered. The solution was concentrated under reduced pressure to afford the title compound as a white solid.

$^1$H NMR d (CDCl$_3$) 7.28 (s, 1H), 7.05 (d, 1H), 6.77 (m, 5H), 6.52 (m, 3H), 5.90 (m 2H), 4.87 (d, J=7.5 Hz, 1H), 4.47 (d, J=7.5 Hz, 1H), 3.80 (m, 2H), 3.80 (s,3H), 1.75 (q, J=7 Hz, 2H), 1.0 (t, J=7 Hz,3H).

EXAMPLE 19
(+) (1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylic acid ethylene diamine salt (2:1)

To 463.0 g (21.7% wt/wt, 203.8 mmol) of a toluene solution of methyl-(1S, 2R, 3S)-3-(2-hydroxy-4-methoxyphenyl)-1-(3,4-methylenedioxyphenyl)-5-(prop-1-yloxy)indane-2-carboxylate was added 425 mL of toluene, 70 g (496 mmol) of potassium carbonate and 183 g (2.04 mol) of ethylene carbonate. The resulting mixture was heated to approximately 110° C. over a period of 60 minutes then held at this temperature. The progress of the reaction was monitored by HPLC. The reaction was considered complete when less than 1.0% PAR (peak area ratio) of starting material was detected. After approximately 3 hours at or around 110° C., the reaction was cooled to 70° C. and DI water (700 mL) was added. The mixture was stirred for 15 minutes then the aqueous layer was separated. The organic layer was washed 5% aqueous citric acid solution (500 mL) followed by DI water (500 mL). The organic phase was separated then concentrated under reduced pressure to a viscous oil. The concentrate was diluted with methanol (300 mL) and tetrahydrofuran (500 mL) then a solution of lithium hydroxide monohydrate (28 g, 654 mmol) dissolved in 300 mL of deionized water was added. The resulting solution was heated to reflux (internal temperature 62–65° C.) over approximately 15 minutes and maintained at reflux while monitoring the reaction progress by HPLC. The reaction was considered complete when no intermediates were detected by in-process HPLC analysis. After approximately 12 hours at reflux the reaction was considered complete and the resulting mixture cooled to ambient temperature. DI water (500 mL) was added and the reaction mixture concentrated under reduced pressure to a volume of approximately 1 L. Toluene (760 mL) followed by citric acid (150 g, 833 mmol) was added to the resulting solution and the mixture stirred for 5 minutes. The bottom aqueous layer was drained and the organic layer was washed twice with aqueous brine solution (600 mL). The organic layer was separated and filtered to afford 868.8 g of (+)(1S,2R,3S)]-3-[2 -(2-hydroxyeth-1-yloxy)-4-methoxyphenyl]-1-(3,4-methylendioxyphenyl)-5-propoxyindane-2-carboxylic acid as a solution in toluene. HPLC wt/wt assay indicated 11.2% wt/wt (+)(1S,2R,3S)]-3-[2-(2-hydroxyeth-1-yloxy)-4-methoxyphenyl]-1-(3,4-methylendioxyphenyl)-5-(prop-1-yloxy)indane-2-carboxylic acid. An analytical sample could be obtained by concentration of the toluene in vacuo and recrystallization from 2-propanol. m.p. 125–127° C. A toluene solution of (+)(1S,2R,3S)]-3-[2-(2-hydroxyeth-1-yloxy)-4-methoxyphenyl]-1-(3,4-methylendioxyphenyl)-5-(prop-1-yloxy)indane-2-carboxylic acid (868.8 g @ 11.2% wt/wt, 192.5 mmol) was concentrated under reduced pressure to a volume of approximately 200 mL. Distillation was discontinued and 2-propanol (500 mL) added to the concentrate. The organic solution was concentrated again under reduced pressure to a volume of approximately 200 mL. Distillation was discontinued and 2-propanol (500 mL) added to the concentrate. The resulting solution in 2-propanol was allowed to stir at ambient temperature for approximately 15 minutes to obtain a homogeneous mixture then diluted with an additional 1000 mL of 2-propanol. The resulting solution was heated to approximately 60° C. over a period of 15–20 minutes under a gentle purge of nitrogen. Heating was discontinued and ethylene diamine (11.6 g, 99.5+%, 192.5 mmol) was added. The reaction mixture was cooled to 30–35° C. over a period of 4 hours. As the solution cooled to 57° C., precipitation of the title compound occurred. The resulting slurry was stirred at ambient temperature for approximately 12 hours then cooled to 0° C. an additional 3 hours before isolation of the title compound via filtration. The product was washed with 3 portions of 2-propanol (300 mL) followed by hexane's (600 mL) chilled to 0–5° C. The product was dried in the vacuum oven for approximately 16 hours at 20–25° C. to afford 91.6 (87%) of the title compound. Anal Calcd. for C30H34NO8 C, 67.15; H, 6.39; N, 2.61. Found, C, 67.2; H,6.48; N, 2.67.

EXAMPLE 20
Methyl-(1S,2R,3S)-3-[2-(2-hydroxyeth-1-yloxy)-4-methoxyphenyl]-1-(3,4-methylenedioxyphenyl)-5-propoxyindane-2-carboxylate This intermediate was isolated by flash column chromatography (SiO$_2$, EtOAc/Hexane=30/70) of a sample of the crude reaction mixture from the preparation of (1S, 2R, 3S)-3-[2-(2-Hydroxyeth-1-yloxy)-4-methoxyphenyl]-1-(3,4-methylendioxyphenyl)-5 -propoxyindane-2-carboxylic acid described above prior to the saponification with lithium hydroxide.

$^1$H NMR (CDCl$_3$), d 7.13 (1H, d, J=9 Hz), 6.86–6.71 (5H, m), 6.52–6.45 (3H, m), 5.94 (2H, s), 5.02 (1H, s), 4.50 (1H, d, J=12 Hz), 3.99–3.90 (3H, m), 3.84–3.75 (4H, m), 3.56 (3H, s), 1.74 92H, qr, J=6 Hz, 15 Hz), 0.98 (3H, t, J=6Hz). MS for C$_{30}$H$_{32}$O$_8$: ESI/MS m/z 521(M+1)$^+$, 489 (M+1-CH$_3$OH), 353, 321, 311, 293, 251.

EXAMPLE 21
Preparation of (+)-methyl-(1S,2S,3S)-5-Propoxy-1-(3,4-methylenedioxy-phenyl)-3-(2-carbomethoxy]methoxy-4-methoxyphenyl)indane-2-carboxylate A 5 L 3 necked round-bottom flask equipped with an air driven stirrer, and a nitrogen inlet/outlet was charged with 212.0 g (98.4% wt/wt, 437.8 mmol) of methyl-(1S,2S,3S)-1-(3,4-methylenedioxyphenyl)-3-(4-methoxy-2-hydroxyphenyl)-5-propoxyindane-2-carboxylate, 2120 mL of acetone and 212 mL of methanol. The resulting slurry/solution was degassed for approximately 10 minutes under house vacuum. After releasing the vacuum and flushing the flask with nitrogen, 302.5 g (2.19 moles) of potassium carbonate followed by 87.1 g (546.6 mmol) of methyl bromoacetate were added in single portions. The resulting slurry was stirred at ambient temperature under an atmosphere of nitrogen while the progress of the reaction was monitored by HPLC. The reaction was deemed to be complete when all the starting material had been converted to the title compound. The slurry was filtered through 300 g of Aluminium oxide rinsing with 1250 mL of acetone. The resulting filtrate was concentrated under reduced pressure to a volume of approximately 500 mL. The concentrate was diluted with 2000 mL of t-butyl methyl ether (TBME) then washed with 2×1000 mL portions of 5% aqueous citric acid followed by 1000 mL of saturated aqueous brine to afford 1720 g of the title compound as a solution in TBME. Analysis indicated 15.6% wt/wt and 98.5% PAR by HPLC. An analytical sample could be obtained by crystallization of a concentrate from a mixture of hexane's and TBME.

$^1$H NMR (CDCl$_3$), d 7.36 (d, 1 H), 7.07 (d, 1 H), 6.73–6.88 (m, 5 H), 6.49 (q, 1H), 6.37 (d, 1H), 5.94 (s, 2H), 5.17 (d, 1 H), 4.68–4.74 (m, 3 H), 4.02 (t, 1H), 3.90 (t, 2H), 3.81 (s, 3H), 3.75 (s, 3H), 2.97 (s, 3H), 1.75–1.87 (m, 2H), 1.0 (t, 3H ) ppm.

EXAMPLE 22
Preparation of (+)-methyl-(1S,2R,3S)-5-Propoxy-1-(3,4-methylenedioxy-phenyl)-3-(2-[carbomethoxy]methoxy-4-methoxyphenyl)indane-2-carboxylate A 1 L 3 necked round-bottom flask equipped with an air driven stirrer, and a nitrogen inlet/outlet was charged with 49.0 g (102.8. mmol) of methyl-(1S,2R,3S)-1-(3,4-methylenedioxyphenyl)-3-(4-methoxy-2-hydroxyphenyl)-5-propoxyindane-2-carboxylate, 490 mL of acetone, 71.0 g of potassium carbonate and 17.3 g (110 mmol) of methyl bromoacetate. The resulting slurry was stirred at ambient temperature under an atmosphere of nitrogen while the progress of the reaction was monitored by HPLC. The reaction was deemed to be complete when all the starting material had been converted to the title compound. The slurry was filtered through 50 g of Aluminium oxide rinsing with 1250 mL of acetone. The resulting filtrate was concentrated under reduced pressure to a volume of approximately 100 mL. The concentrate was diluted with 500 mL of t-butyl methyl ether then washed with 2×300 mL portions of 5% aqueous citric acid followed by drying over anhydrous magnesium sulphate. The resulting solution was concentrated under reduced pressure to afford 49.2 g of the title compound as an oil. HPLC analysis indicated 97.8% PAR.

$^1$H NMR (CDCl$_3$) of the crude material, d 7.13 (d, 1 H), 6.69–6.82 (m, 5 H), 6.48–6.56 (m, 2 H), 6.36 (d, 1H), 5.94 (s, 2H), 4.98 (d, 1 H), 4.5–4.65 (m, 3 H), 3.7–3.85 (m, 8 H), 3.6 (s, 3H), 3.33 (t, 1 H), 1.68–1.80 (m, 2H), 1.0 (t, 3H ) ppm.

It will be appreciated by those skilled in the art that changes could be made to the embodiments described above without departing from the broad inventive concept thereof. It is understood, therefore, that the invention is not limited to the particular embodiments disclosed, but it is intended to cover modifications within the spirit and scope of the present invention as defined by the appended claims.

What is claimed is:

1. The process for preparing the compound:

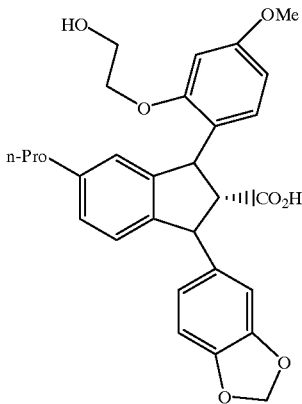

(+) (1S, 2R, 3S)-3-[2-hydroxyeth-1-yloxy)-4-methoxyphenyl]-1-(3,4-methylenedioxyphenyl)-5-(prop-1-yloxy)indane-2-carboxylic acid;

which comprises:

(a) mixing 2-bromo-4-methoxyphenol dissolved in DME/THF with a base to form the corresponding phenoxide (b) reacting the product of (a) with effective amounts of 2,3,:5,6-di-O-isopropylidene-α-D-mannofuranosyl halide in DME/THF at a temperature ranging from about room temperature to the reflux temperature of the solvent to form 2-bromo-5-methoxyphenyl-2,3:5,6-di-O-isopropylidene-α-D-mannofuranoside;

(c) forming the Grignard reagent of the product of (b);

(d) reacting the Grignard reagent of step (c) with an effective amount of methyl 3-(3,4-methylenedioxyphenyl)-6-(prop-1-yloxy)-1-oxo-indene-2-carboxylate in an inert solvent to form the diasteromeric compounds (R) and (S)-methyl [2,3:5,6-di-O-isopropylidene-α-D-mannofuranosyloxy-4-methoxyphenyl]-6-propoxy-1H-indene-2-carboxylate;

(e) dissolving the products of (d) in n-butanol and crystallizing and recovering the R isomer therefrom;

(f) hydrogenating the product of (e) with hydrogen gas in the presence of a basic or neutral hydrogenation catalyst comprising about 10% to about 15% of palladium on carbon at a pressure ranging from about 80 psi to about 110 psi;

(g) treating the product of (f) with Bronsted acid to from the corresponding phenol;

(h) alkylating the product of (g) with ethylene carbonate under alklyating conditions; and (i) hydrolyzing the product of (h).
2. The process for preparing the compound:

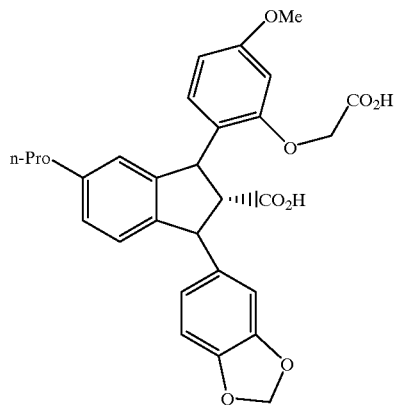

(+)-(1S, 2R, 3S)-3-(2-carboxymethoxy-4-methoxyphenyl)-1-(3,4-methylenedioxyphenyl)-5-(prop-1-yloxy)indane-2-carboxylic acid;
which comprises:

(a) mixing 2-bromo-4-methoxyphenol dissolved in DME/THF with a base to form the corresponding phenoxide;

(b) reacting the product of (a) with effective amounts of 2,3,:5,6-di-O-isopropylidene-α-D-mannofuranosyl halide in DME/THF at a temperature ranging from about room temperature to the reflux temperature of the solvent to form 2-bromo-5-methoxyphenyl-2,3:5,6-di-O-isopropylidene-α-D-mannofuranoside;

(c) forming the Grignard reagent of the product of (b);

(d) reacting the Grignard reagent of step (c) with an effective amount of methyl 3-(3,4-methylenedioxyphenyl)-6-(prop-1-yloxy)-1-oxo-indene-2-carboxylate in an inert solvent to form the diasteromeric compounds (R) and (S)-methyl [2,3:5,6-di-O-isopropylidene-α-D-mannofuranosyloxy-4-methoxyphenyl-6-propoxy-1H-indene-2-carboxylate;

(e) dissolving the products of (d) in n-butanol and crystallizing and recovering the R isomer therefrom;

(f) hydrogenating the product of (e) with hydrogen gas in the presence of a basic or neutral hydrogenation catalyst comprising about 10% to about 15% of palladium on carbon at a pressure ranging from about 80 psi to about 110 psi;

(g) treating the product of (f) with Bronsted acid to from the corresponding phenol;

(h) alkylating the product of (g) with $L_1(CH_2)CO_2R_{13}$ under alkylating conditions; wherein L is Br, Cl, I, tosylate or mesylate and $R_{13}$ is $C_1$–$C_5$ alkyl, and (i) hydrolyzing the product of (h).

3. The process according to claim 1 wherein the base added in (a) is lithium hydroxide, sodium hydroxide, potassium hydroxide, sodium $C_1$–$C_5$ alkoxide, potassium $C_1$–$C_5$ alkoxide, DBU, sodium hydride, potassium hydride, lithium bis(trimethylsilylamide), n-butyl lithium, t-butyl lithium or sec-butyl lithium.

4. The process according to claim 3 wherein at least one molar equivalent of the base is added per mole of 2-bromo4-methoxyphenol.

5. The process according to claim 1 wherein the temperature in step (b) ranges from about 50° C. to about 120° C.

6. The process according to claim 1 wherein the Grignard reagent is formed by reacting a $C_1$–$C_5$ alkyl lithium at a temperature of less than about 0° C. in a second inert solvent optionally containing an additive and treating the resultant product with a magnesium halide at a temperature ranging from less than about −70° C. to about 25° C., wherein halide is bromide, chloride or iodide.

7. The process according to claim 6 wherein the second inert solvent is tetrahydrofuran, toluene, heptane, or hexane.

8. The process according to claim 6 wherein the additive is selected from the group consisting of N,N,N',N'-tetramethylene diamine and N,N'-dimethylpropylurea.

9. The process according to claim 1 wherein the reaction of the Grignard reagent in step (d) is conducted at a temperature of less than about −70° C.

10. The process according to claim 1 wherein step (e) comprises dissolving and stirring in n-butanol at a temperature ranging from about 50° C. to about 60° C. cooling to initiate crystalization and then cooling the solvent containing said crystals to about room temperature or below until sufficient time for crystallization of the predominant diasteromer is completed and recovering the crystalline product.

11. The process according to claim 1 wherein the hydrogenation reaction is conducted at a temperature ranging from about 15° C. to about 50° C.

12. The process according to claim 1 wherein the pH of the hydrogenation reaction of step (f) ranges from about 6.3 to 7.5.

13. The process according to claim 2 wherein the base added in (a) is lithium hydroxide, sodium hydroxide, potassium hydroxide, sodium $C_1$–$C_5$ alkoxide, potassium $C_1$–$C_5$ alkoxide, DBU, sodium hydride, potassium hydride, lithium bis(trimethylsilylamide), n-butyl lithium, t-butyl lithium or sec-butyl lithium.

14. The process according to claim 13 wherein at least one molar equivalent of the base is added per mole of 2-bromo-4-methoxyphenol.

15. The process according to claim 2 wherein the temperature in step (b) ranges from about 50° C. to about 120° C.

16. The process according to claim 2 wherein the Grignard reagent is formed by reacting a $C_1$–$C_5$ alkyl lithium at a temperature of less than about 0° C. in a second inert solvent optionally containing an additive and treating the resultant product with magnesium halide at a temperature ranging from less than about −70° C. to about 25° C., wherein halide is bromide, chloride or iodide.

17. The process according to claim 16 wherein the second inert solvent is tetrahydrofuran, toluene, heptane, or hexane.

18. The process according to claim 16 wherein the additive is selected from the group consisting of N,N,N',N'-tetramethylene diamine and N,N'-dimethylpropylurea.

19. The process according to claim 2 wherein the reaction of the Grignard reagent in step (d) is conducted at a temperature of less than about −70° C.

20. The process according to claim 2 wherein step (e) comprises dissolving and stirring in n-butanol at a temperature ranging from about 50° C. to about 60° C. cooling to initiate crystalization and then cooling the solvent containing said crystals to about room temperature or below until sufficient time for crystallization of the predominant diasteromer is completed and recovering the crystalline product.

21. The process according to claim 2 wherein the hydrogenation reaction is conducted at a temperature ranging from about 15° C. to about 50° C.

22. The process according to claim 2 wherein the pH of the hydrogenation reaction of step (f) ranges from about 6.3 to 7.5.

* * * * *